(12) United States Patent
Ray et al.

(10) Patent No.: US 11,857,632 B1
(45) Date of Patent: Jan. 2, 2024

(54) NANOCELLULOSE AS AN EMBEDDING MATRIX AND APPLICATIONS THEREOF

(71) Applicant: INNOSENSE LLC, Torrance, CA (US)

(72) Inventors: Anamika Ray, Torrance (CA); Cheyann Wetteland, Madison, WI (US); Harini Madakashira, Allen, TX (US); Joseph Kessler, Fullerton, CA (US); Uma Sampathkumaran, Torrance, CA (US)

(73) Assignee: INNOSENSE LLC, Torrance, CA (US)

( * ) Notice: Subject to any disclaimer, the term of this patent is extended or adjusted under 35 U.S.C. 154(b) by 0 days.

(21) Appl. No.: 16/663,335

(22) Filed: Oct. 24, 2019

(51) Int. Cl.
| | |
|---|---|
| *A61K 47/38* | (2006.01) |
| *A61L 27/20* | (2006.01) |
| *A61L 27/52* | (2006.01) |
| *A61K 47/40* | (2006.01) |
| *B82Y 5/00* | (2011.01) |
| *B82Y 30/00* | (2011.01) |
| *B82Y 40/00* | (2011.01) |

(52) U.S. Cl.
CPC .............. *A61K 47/38* (2013.01); *A61K 47/40* (2013.01); *A61L 27/20* (2013.01); *A61L 27/52* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

2019/0192539 A1* 6/2019 Song .................... A61K 9/7007

FOREIGN PATENT DOCUMENTS

CN 109081927 * 7/2020

OTHER PUBLICATIONS

Masruchin et al. "Characteristics of TEMPO-oxidized cellulose fibril-based hydrogels induced by cationic ions and their properties". 2015.*
France et al. "Review of Hydrogels and Aerogels Containing Nanocellulose" 2017.*
Kayra et al. "Synthesis of Cellulose-Based Hydrogels, Preparation, Formation, Mixture and Modification" 2018.*
Ahumada et al. "Porosity in Biomaterials: A Key Factor in Development of Applied Materials in Biomedicine" Feb. 14, 2019.*
Goi et al. "Dual Functions of TEMPO-oxidized cellulose Nanofibers in Oil-in water Emulsions: A piercing Emulsifier and a Unique Dispersion stabilizer" (Jul. 2019).*
Kun et al. "Injectable Supramolecular hydrogels for Insulin Delivery". 2017.*

* cited by examiner

*Primary Examiner* — Danah Al-Awadi
(74) *Attorney, Agent, or Firm* — Polson Intellectual Propery Law, PC; Margaret Polson

(57) ABSTRACT

A versatile drug delivery system comprised of plant-based nanocellulose can be used for providing high loading and extended release for virtually any drug. This system is made from nanocrystalline cellulose chemically cross-linked to form a hydrogel. This versatile hydrogel-based drug delivery system can be functionalized to support extended release of oral dosing, relieving patient burden and increasing quality of life.

9 Claims, 19 Drawing Sheets

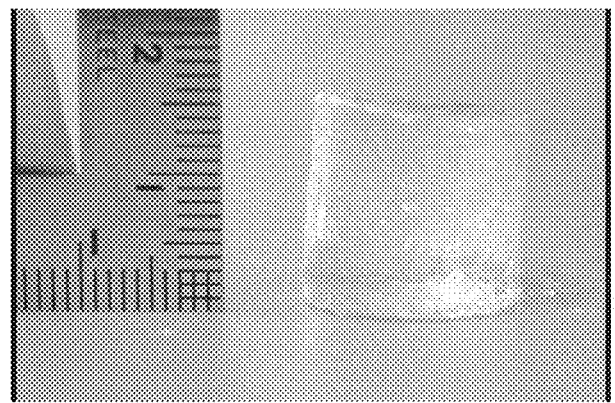
FIGURE 13A
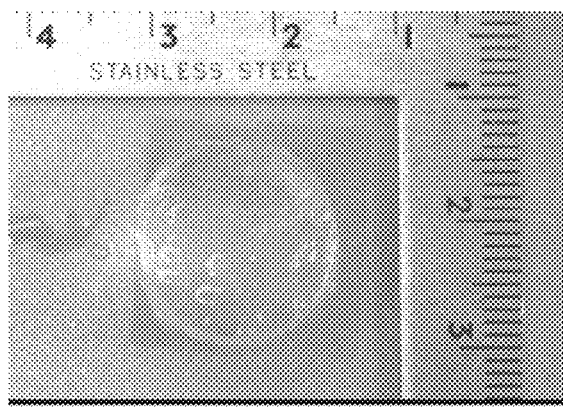 
FIGURE 13B          FIGURE 13C

NANOCELLULOSE AS AN EMBEDDING MATRIX AND APPLICATIONS THEREOF

Inventions described herein were made with government support under Department of Energy (DOE; Award No. DE-SC0018014) and Department of Defense (CBD-DoD; Award no. W911QY-18-C-0200). The US Government may have certain rights in the inventions described herein.

FIELD OF THE INVENTION

The present invention relates to a versatile nanocellulose-derived hydrogel drug delivery system and a novel excipient for providing extended release in oral dosing pharmaceuticals.

BACKGROUND

Therapeutic drug dosing for chronic diseases or other conditions can create intense burden for patients and caregivers. Oral dosing has the highest rate of compliance amongst patients due to ease of use. However, for drugs that require frequent dosing, the oral dosing can interfere with sleep schedules or can be forgotten. To improve patient compliance, sustained delivery of such drugs is ideal. However, most sustained drug delivery mechanisms rely on injections or implants. By developing an oral delivery system for sustained drug release, patient compliance and therapeutic treatment efficacy can be improved. Hydrogels can provide sustained drug delivery and have been investigated for a variety of drug delivery applications. (Kiuchi I S, Cardoso Galante R S, Dua K, Malipeddi V R, Awasthi R, Ghisleni DDM, de Jesus Andreoli Pinto T. "Hydrogel Based Drug Delivery Systems: A Review with Special Emphasis on Challenges Associated with Decontamination of Hydrogels and Biomaterials" *Current Drug Delivery.* 2017; 14(7, pp: 917-925; Gu D, O'Connor A J, G H Qiao G, Ladewig K. "Hydrogels With Smart Systems For Delivery Of Hydrophobic Drugs." *Expert Opinion on Drug Delivery,* 2017, 14(7), pp. 879-895; Gao W, Zhang Y, Zhang Q, Zhang L. "Nanoparticle-Hydrogel: A Hybrid Biomaterial System for Localized Drug Delivery". *Annals of Biomedical Engineering,* 2016. 44(6), pp. 2049-2061). Cellulose, a biofeedstock polymer, is the most abundant naturally occurring polymer on earth. Use of biofeedstock provides a natural, bioabsorbable and environmentally friendly alternative to conventional hydrogels.

The self-assembly properties of nanocellulose obtained from cellulose offer numerous applications. In particular, utilization of cellulose nanocrystals (CNC) and cellulose nanofibers (CNF) as drug excipients is a promising area for replacing petroleum-based products. Nanocellulose can be functionalized readily by its hydroxyl handle, allowing versatile chemistry. Additionally, it is inexpensive, biocompatible and biodegradable, making it highly advantageous for use in drug delivery. (Lin N, Dufresne A. "Nanocellulose in Biomedicine: Current Status and Future Prospect", *European Polymer Journal* 2014, 59, pp. 302-25; Habibi Y, Lucia L A, Rojas O J. "Cellulose Nanocrystals: Chemistry, Self-Assembly, and Applications", *Chemical Reviews,* 2010, 110 (6), pp. 3479-500; Klemm D, Kramer F, Moritz S, Lindstrom T, Ankerfors M, Gray D, et al., "Nanocelluloses: A New Family of Nature-Based Materials", *Angewandte Chemie-International Edition,* 2011, 50(24), pp. 5438-66; Börjesson M, Westman G. "Cellulose—Fundamental Aspects and Current Trends", *InTech,* 2015.)

Also, the market for protein-based and small molecule-based pharmaceuticals is growing and would benefit from advancements in (1) structural stability (2) intestinal absorption (3) sustained release and (4) bio-based carrier platforms. Inherent chemistry, safety, and low-cost render nanocellulose as a promising drug excipient material. Supramolecular nanocellulose drug excipients have sustained release, which would reduce dosing frequency and increase patient compliance. Nanocellulose excipients also have large surface area to volume ratios affording a large payload for further dose control.

By functionalizing the hydroxyl handle, CNC may bind to hydrophobic or hydrophilic drugs. CNC, produced through acid hydrolysis without further functionalization, can bind protein drug targets directly and facilitate oral drug delivery of over 130 Food and Drug Administration (FDA)-approved peptide-based therapeutics. (Bruno B J, Miller G D, Lim C S, "Basics and Recent Advances in peptide and Protein Drug Delivery.", *Ther. Deliv,* 2013, 4(11), pp. 1443-6'7; Muheem A, Shakeel F, Jahangir M A, Anwar M, Mallick N, Jain G K, et al. "A Review On The Strategies For Oral Delivery Of Proteins And Peptides And Their Clinical Perspectives", *Saudi Pharmaceutical Journal,* 2016, 24(4); pp. 413-28)

In the drug delivery sector, nanocellulose based wound dressings are commercially available, ("Suprasorb", http://www.lohmann-rauscher.com/en/products/wound-care/moist-wound-management.html), but oral drug delivery agents have not yet been marketed. Oral drug delivery with controlled or sustained release is a preferred route of administration for many drugs due to increased patient compliance and reduction of resources necessary (i.e., no syringes or trained personnel needed). A sustained or controlled release system reduces the dosing frequency, which provides more uniform circulation and reduction in drug side-effects. Other macro-cellulose based materials are widely used commercially for fillers in drugs. Crystalline nanocellulose is known to have low ecotoxicity and cytotoxicity. In particular, CNC for oral drug delivery of various hydrophilic and hydrophobic drugs in research literature shows favorable stability and controlled release. (Jackson J K, Letchford K, Wasserman B Z, Ye L, Hamad W Y, Burt H M, "The Use of Nanocrystalline Cellulose for the Binding and Controlled Release of Drugs", *International Journal of Nanomedicine* 2011, 6, pp. 321-30; Guo J, Catchmark J M, Mohamed M N A, Benesi A J, Tien M, Kao T H, et al., "Identification and Characterization of a Cellulose Binding Heptapeptide Revealed by Phage Display", *Biomacromolecules* 2013, 14(6), pp. 1795-805; Zhang X L, Huang J, Chang P R, Li J L, Chen Y M, Wang D X, et al. "Structure and Properties of Polysaccharide Nanocrystal-doped Supramolecular Hydrogels based on Cyclodextrin Inclusion", *Polymer* 2010, 51(19), pp. 4398-407; Jorfi M, Foster E J., "Recent Advances in Nanocellulose for Biomedical Applications", *Journal of Applied Polymer Science* 2015; 132(14))

CNC-based excipient materials are derived from a biodegradable, renewable source that does not compete with food availability. CNC is produced by sulfuric acid hydrolysis (65% w/w) of cellulose, generally from wood pulp. The amorphous regions are acid hydrolyzed leaving the crystalline regions intact. High purity crystalline nanocellulose is produced in small quantities by several commercial sources operating pilot plants. The continued growth in production will support numerous nanocellulose applications.

The recovery of acid used for CNC production and the fate of the amorphous cellulose fractions should also be considered in the production. At the pilot plant scale (e.g. Forest Product Laboratory (FPL)), it is not economical to recover the acid, whereas larger commercial scale plants do recover the acid. However, it is unclear from the published documents if the hemicellulose portions are recovered, but it is conceivable that the amorphous acid-digested hemicellulose (approximately 20% of the total cellulose) could be recovered by methods such as that described by Pirani, et al., and utilized for biofuel production (Pirani S, Hashaikeh R. "Nanocrystalline Cellulose Extraction Process and Utilization of the Byproduct for Biofuels Production." *Carbohydr Polym* 2013, 93(1), pp. 357-363)

CNC retains many hydroxyl groups on the glucose monomers, providing a highly reactive surface. Additionally, there is a negative charge arising from sulfation of a fraction of the hydroxyl groups during sulfuric acid hydrolysis (CNC sulfur content<1%). Negative surface sulfate esters, $-OSO_3^-$, on CNC form during sulfuric acid ($H_2SO_4$) hydrolysis via condensation esterification between the hydroxyl group and the $H_2SO_4$. This negative charge imparts electrostatic interactions with molecules such as proteins. Thus, protein drugs can electrostatically adsorb or chemically conjugate to the CNC (Lin, N., ibid.; Guo, J. ibid.). Hydrogels formed by nanocellulose have shown high loading (>100% w/w) and good release kinetics (>48 h) for bovine serum albumin as a model protein. (Börjesson, M, Ibid.; Zhang, XL, Ibid.; Muller A, Ni Z X, Hessler N, Wesarg F, Muller F A, Kralisch D, et al., "The Biopolymer Bacterial Nanocellulose as Drug Delivery System: Investigation of Drug Loading and Release using the Model Protein Albumin", *Journal of Pharmaceutical Sciences* 2013, 102(2), pp. 579-592). CNC demonstrates controlled release (>7 h) in simulated body fluid showing that CNC acts as a diffusion barrier and facilitates controlled release. (Börjesson, M, Ibid.)

A composite hydrogel with CNC-bovine serum albumin (BSA) demonstrated sustained release>48 hr. (Zhang, XL, Ibid.) Similar bacterial nanocrystalline hydrogels also demonstrated promising results. For example, BSA and luciferase undergo a burst release (~8 h), then sustained release for over 48 h. (Muller. A, Ibid.) CNC has been more widely studied for drug delivery of various hydrophilic and hydrophobic drugs in research literature and shows good stability and controlled release (48 h) (Lin, N., Ibid.; Jackson, J K, Ibid.; Guo, J., Ibid; Zhang, X L., Ibid; Jorfi, M., Ibid).

For oral delivery, wide pH stability is imperative. The low pH of the stomach (as low as 1-2) does not affect the integrity nor release kinetics of protein from nanocellulose hydrogels. (Muller. A, Ibid.; Chung Y C, Shyu Y. "The Effects of pH, Salt, Heating and Freezing on the Physical Properties of Bacterial Cellulose—nata". International *Journal of Food Science and Technology* 1999; 34(1), pp. 23-26).

The inherent chemistry of the CNC demonstrated in these numerous studies on small molecule drug and model proteins exhibit good pH stability/biostability, electrostatic absorption of protein drugs for high loading, and diffusion-controlled release.

Oral delivery of protein drugs is preferred due to ease of administration and increased effectiveness of treatment. However, technical difficulties, including acid-catalyzed degradation in the stomach (~2 h exposure), absorption through intestinal epithelial cell barrier, proteolytic breakdown, and protein stability present issues which interfere with effective oral drug delivery. (Chaturvedi K, Ganguly K, Nadagouda M N, Aminabhavi T M. "Polymeric Hydrogels for Oral Insulin Delivery", *Journal of Controlled Release* 2013, 165(2), pp. 129-38).

SUMMARY

It is an object of the embodiments set forth herein to provide extended release compositions for an oral dosing drug delivery system that can deliver pharmaceuticals of different types and molecular sizes including hydrophilic small molecule drugs and hydrophobic proteins.

It is also an object of the present invention to provide methods for modifying (tuning) CNC and CNF hydrogel formulations to deliver compounds of different types and molecular sizes in a controlled manner. In particular, it is an object of systems and materials described herein to provide a versatile cellulose-based drug delivery system for delivery of both hydrophobic and hydrophilic drugs for extended controlled release for oral dosing. The drug delivery system described herein has been tested in in vivo release studies, as well as in vitro studies for both kinetic assays, and histopathological studies. A large quantity of drug, for example 250 mg of drug per cubic centimeter, can be loaded into each hydrogel was readily achieved, said drug them released in a controlled preset manner.

BRIEF DESCRIPTION OF DRAWING

Further features of the invention, its nature and various advantages will be more apparent from the accompanying drawings and the following detailed description of the preferred embodiments, in which:

FIG. 2A shows hydration of CNC with stirring and heating, resulting in a viscous suspension shown in FIG. 2B.

FIG. 3A shows unmodified-CNF (UM-CNF) being hydrated under high-powered sonication. Resulting in a clear solution (FIG. 3B). FIG. 3C illustrates the hydrogel that formed after addition of a solution of a metal-ion salt.

FIG. 13A shows the TEMPO-oxidized cellulose hydrogel from FIG. 3C in two different fluids and FIGS. 13B and 13C show the result of soaking the sample of FIG. 13A in two different fluids. FIG. 13B shows the hydrogel after soaking in PBS for 7 days; FIG. 13C shows the hydrogel after soaking in deionized water for 7 days.

FIG. 18A is the DSC for commercial cellulose powder; FIG. 18B is the DSC for hydrogel made with commercial cellulose powder and FIG. 18C is the DSC for gel from 18B after freeze drying.

FIG. 19A is the DSC for Pyridostigmine Bromide (PB) powder and FIG. 19B is the DSC for Hydrogel with PB encapsulated therein.

FIG. 20A illustrates the total amount of PB released after an allotted time and FIG. 20B illustrates the rates of release at different time points for the different concentrations of NaOH hydrogels.

FIG. 21A shows the kinetic release profile of free PB into a PBS solution and FIG. 21B shows the rate of release of encapsulated PB from hydrogel versus time.

FIG. 25A shows a PB dosage study and FIG. 25B shows a CNC-PB dosage MTD study.

DETAILED DESCRIPTION

Figure 1:
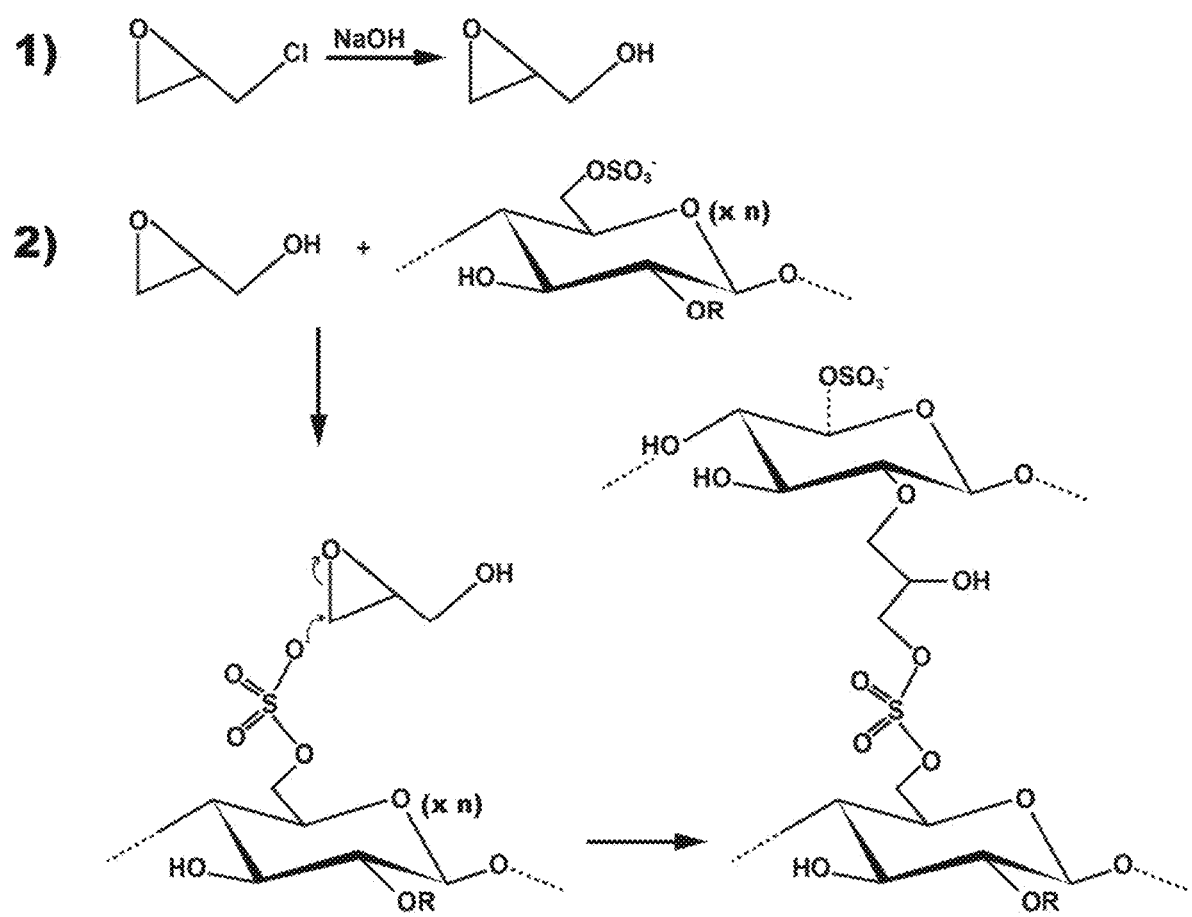
FIG. 1 shows an overview of the epichlorohydrin reaction with cellulose sulfate to make hydrogels.

Crystalline nanocellulose offers high protein stability, good release profile and high drug loading, with increased bioavailability via additives like cyclodextrin. The CNC content can be tailored to control diffusion kinetics. There are numerous chemical functionalities that can be introduced via the hydroxyl groups to provide appropriate surface chemistry. Embodiments described herein also utilize the electrostatic interactions between the proteins and the negative sulfate esters on CNC formed during acid hydrolysis.

CNC self-assembles to form a fibrous network with a high surface area to volume ratio translating to large binding area. The protein drug electrostatically binds to the nanocellulose and releases over >24 h, controlled by diffusion. The nanocellulose maintains the protein structure, prevents aggregation, and limits environmental exposure. Described below are methods for making unique tunable hydrogels suitable for sustained delivery of several different drug types.

Diabetes affects >9% of the United States population and is treated by insulin protein therapy to reduce blood glucose levels. Generally, the insulin is sourced from porcine or bovine pancreas. This is administered intravenously and significantly reduces morbidity and mortality. However, approximately 60% of patients fail to achieve long-term glycemic control, which may be in part due to low patient compliance. Transdermal or oral delivery has the highest patient adherence.

Insulin oral delivery systems with high loading, sustained release, and good bioavailability are being developed; there are several technologies now in the clinical trial stage. (Fonte P, Araujo F, Reis S, Sarmento B. "Oral Insulin Delivery: How Far Are We?" *J Diabetes Sci Technol*, 2013, 7(2), pp. 520-31). However, many of these developing technologies involve synthetic petroleum-based polymers or they are nanoparticle formulations with unknown physiological side effects. Many of the drug delivery systems also incorporate absorption enhancers that are not protein specific which increases the risk of absorption of toxins or allergens along with the therapeutic compound. Enzyme inhibitors are also used, but prolonged use may reach high toxicity and may increase the absorption of other proteins that would otherwise be degraded. (Muheem, A., Ibid.; Renukuntla J, Vadlapudi A D, Patel A, Boddu S H S, Mitra A K. "Approaches for Enhancing Oral Bioavailability of Peptides and Proteins", *International Journal of Pharmaceutics*, 2013; 447(1-2); pp. 75-93) The leading oral delivery systems being developed for general protein drugs are the GI-MAPS system (Eudragit®) and SNAC carrier microemulsion (Emisphere™) (Bruno, B J., Ibid.).

GI-MAPS is a gastrointestinal mucoadhesive patch system within an enteric coating that has demonstrated 6-23% bioavailability of a model protein. GI-MAPS system is a multi layer composition containing materials sourced from fossil fuels. (Eiamtrakarn S, Itoh Y, Kishimoto J, Yoshikawa Y, Shibata N, Murakami M, et al. "Gastrointestinal Mucoadhesive Patch System (GI-MAPS) for Oral Administration of G-CSF, a Model Protein", *Biomaterials*, 2002, 23(1), pp. 145-52).

SNAC is a microemulsion system of (n-(8-[2-hydroxyl-benzoyl]amino)caprylic acid) with protein solubilized in the interior that transports the protein drug across the epithelial membrane where the complex dissociates. SNAC delivery demonstrates 5-10% bioavailability but releases the protein as a fast release bolus and not as controlled release for basal insulin levels over prolonged time. (Kidron M, Dinh S, Menachem Y, Abbas R, Variano B, Goldberg M, et al. "A Novel Per-oral Insulin Formulation: Proof of Concept Study in Non-diabetic Subjects", *Diabetic Medicine*, 2004, 21(4), pp. 354-357).

In contrast to the technologies addressed above, the embodiments set forth herein provide a manufacturing process using materials sourced from a bio-feedstock to produce drug carriers with predicted high bioavailability, controlled release time, and superior protein stabilization.

In one or more embodiment, CNC delivery systems set forth herein use hydrogels for delivery of pyridostigmine bromide (PB). Pyridostigmine bromide is the standard pretreatment against the lethal effects of organophosphorus (OP) nerve agent (e.g., soman) exposure, currently the sole Food and Drug Administration (FDA)-approved pretreatment medication to reduce the number of daily administrations of fielded medication with logistical and operational mobility improvements. These embodiments address the Joint Chemical and Biological Defense (CBD) program seeking improved formulations of PB that are functional in austere environments and have sustained release with prolonged drug efficacy. The acute toxicity of nerve agents is attributed to the irreversible binding and inactivation of the enzyme acetylcholinesterase (AChE) leading to accumulation of synaptic acetylcholine (ACh). This leads to persistent and excessive stimulation of acetylcholine receptors resulting in acute cholinergic toxicity. Even if patients receive treatment after OP exposure, most of them suffer from wide ranging physiological sequelae, including seizures, neurodegeneration and psychological deficits.

The prophylactically administered PB acts as a more readily reversible and "temporary" inhibitor of AChE due to its carbamylation of the active site serine. This precludes OP from longer-term and potentially irreversible inactivation of AChE by phosphorylation, thereby mitigating the risks. Thus, PB effectively creates a safety net by providing a pool of transiently bound AChE that is essentially protected and therefore unavailable for the irreversible binding of nerve agents. The recommended PB dose is one 30 mg tablet every 8 hours beginning several hours prior to nerve agent exposure. In humans, this dosing of PB inhibits 20-40% of red blood cell cholinesterase (i.e., AChE). This level of inhibition protects animals from the lethal effects of soman and other OPs. The PB dosages, referred to as Soman Nerve Agent Pretreatment Pyridostigmine (SNAPP), are issued in blister packs of 21 tablets. NSN 6505-01-178-7903 is one pack of 10 blister packs. Prior to issue, these light- and temperature-sensitive hygroscopic tablets must be stored at between 2-8° C. Once issued to a soldier, the PB in the blister pack is usable for up to three months after which it must be discarded. Storage of this tablet formulation at controlled room temperature (25° C.) reduces shelf life. Therefore, an improved and stable formulation is needed to withstand higher temperatures, for example desert temperatures. Based on the current state of military operations and unrest worldwide, there is a need for a nerve agent pretreatment that can be administered less frequently than SNAPP. Such improved formulations could also be administered as a pretreatment for first responders and health care providers following a suspected nerve agent attack or during mass casualty decontamination.

As demonstrated by the capability set forth herein to exhibit sustained release of insulin, a large hydrophobic protein, with a molecular weight less than 50,000 Da, and PB, a hydrophilic small molecule with a molecular weight less than 500 Da, the CNC-based hydrogels described herein provide a tunable excipient for a wide variety of drug types.

The description below outlines the compositions and methods for an oral drug delivery system for sustained delivery of proteins, drugs, and hydrophilic small molecules. The delivery system utilizes porous nano-crystalline or nano-fibrillar cellulose networks to form hydrogels that can be loaded via diffusion or in situ loading during gelation.

An example of nanocellulose hydrogel crosslinking is shown in FIG. 1. Epoxy-terminated crosslinkers, such as epichlorohydrin, can be activated in an alkaline environment and react with available hydroxyl groups. The reaction of epichlorohydrin with cellulose sulfate is activated by NaOH or other bases to make cellulose hydrogels. Then cellulose hydrogels are then reacted with available $OH^-$ or $O^-$ groups to crosslink with other cellulose groups. The result is a highly porous network suitable for holding large proteins. Alternatively, metal ions can also be used to form ion complexation to form very tight hydrogel networks with lower porosity, suitable for smaller drugs.

Figure 2A:
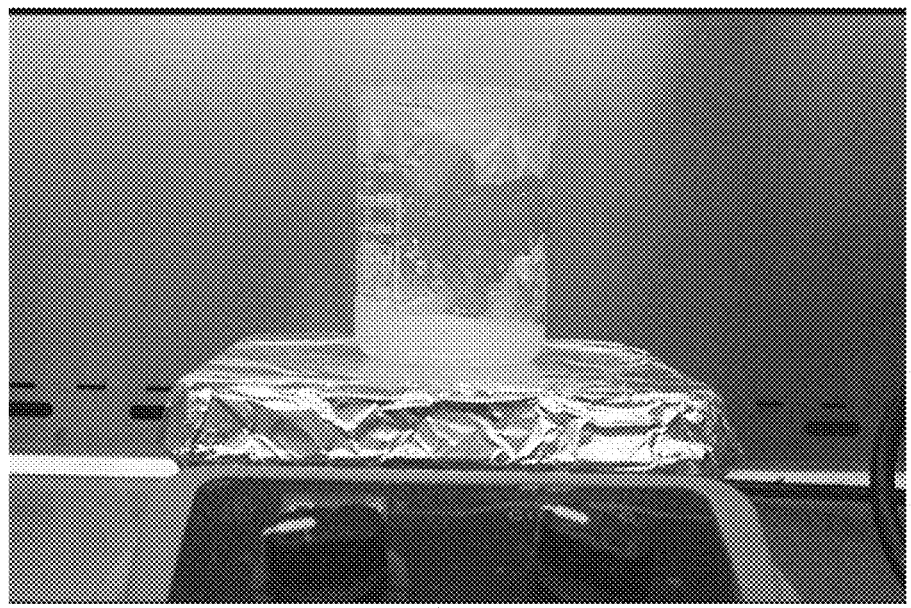
FIGS. 2A and 2B illustrate hydration of CNC to form a viscous suspension of crosslinked sulfated CNC hydrogel.
Figure 2B:
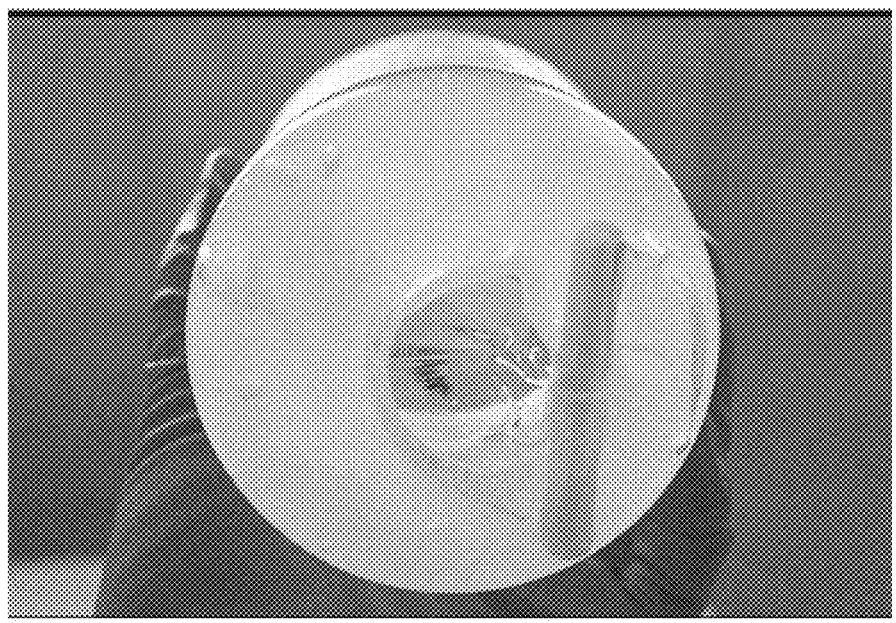
Figures 3A, 3B:
FIGS. 3A, 3B and 3C illustrate steps in the gelation process for TEMPO-(2,2,6,6-tetramethylpiperidine-1-oxyl radical)oxidized CNF using metal ions.

The general processes and results for making hydrogels by chemical crosslinking is shown FIGS. 2A and 2B); the use of metal ion complexation is illustrated in FIGS. 3A and 3B.

With reference to FIGS. 2A and 2B CNC is hydrated via stirring and heating (FIG. 2A), resulting in a viscous suspension (FIG. 2B). Then a basic solution is added, reducing viscosity. Once the solution is homogenous, a chemical crosslinker is added and the mixture is poured into a crystallization dish and let stand overnight. The hydrogel will then hold its shape. The hydrogel is then washed and cut into pieces, such as 16 mm diameter cylinders, which can be removed from the crystallization dish for subsequent processing.

Figure 3C:
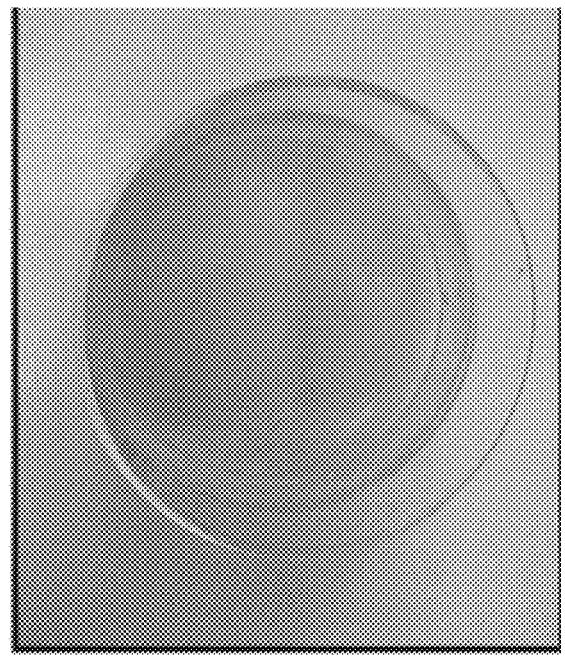

With reference to FIGS. 3A, 3B and 3C unmodified-CNF (UM-CNF) is hydrated under high-powered sonication (FIG. 3A) resulting in a clear solution shown in FIG. 3B. A metal ion salt, such as $Al(NO_3)_3$, is then dissolved in water and added to the UM-CNF mixture which results in rapid gelation, shown in FIG. 3C. The hydrogel is then washed and cut into smaller pieces, such as uniform hydrogel cylinders, for later processing.

The properties of chemically crosslinked hydrogels can be tuned by controlling the following parameters: cellulose source, degree of sulfation or other functionalization, percentage of cellulose, pH, crosslinker selection, amount of crosslinker, and mixing (speed and duration). The properties of metal-ion crosslinked gels can be tuned by metal-ion selection.

Figures 4, 5:
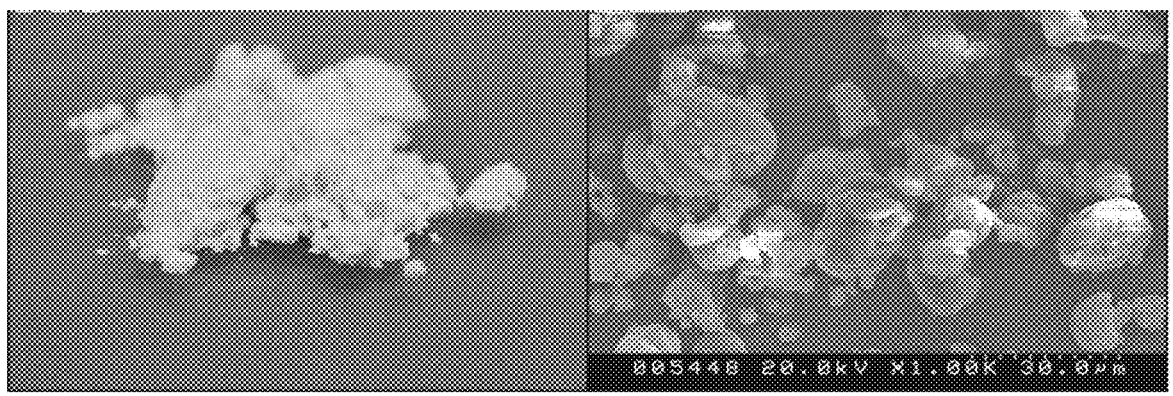
FIG. 4 is a photograph of the source cellulose sulfate material.
FIG. 5 is a scanning electron microscopy (SEM) micrograph showing the structure of the source cellulose sulfate material.
Figures 6, 7:
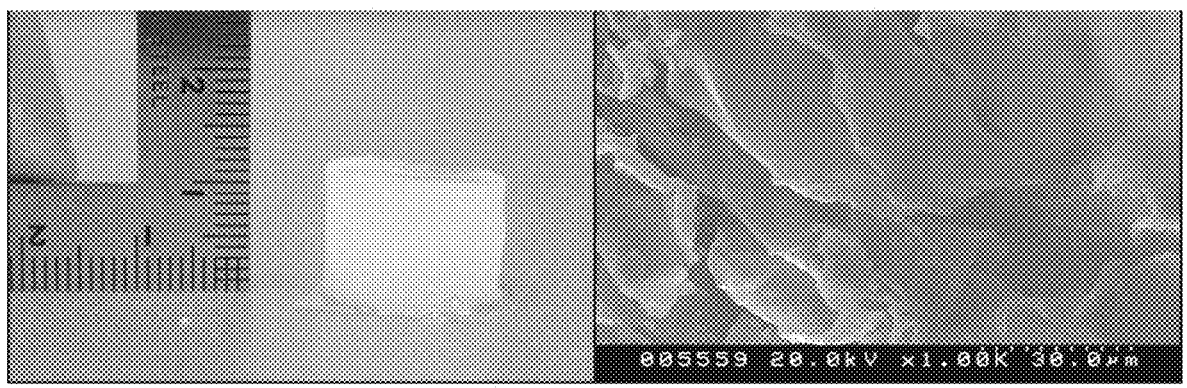
FIG. 6 is a photograph of the hydrogel made from cross-linked cellulose sulfate.
FIG. 7 is a SEM micrograph showing the structure of the cross-linked cellulose sulfate.
Figures 8, 9:
FIG. 8 is a photograph of the source TEMPO-oxidized cellulose.
FIG. 9 is a SEM micrograph of the structure of the source TEMPO-oxidized cellulose.
Figures 10, 11:
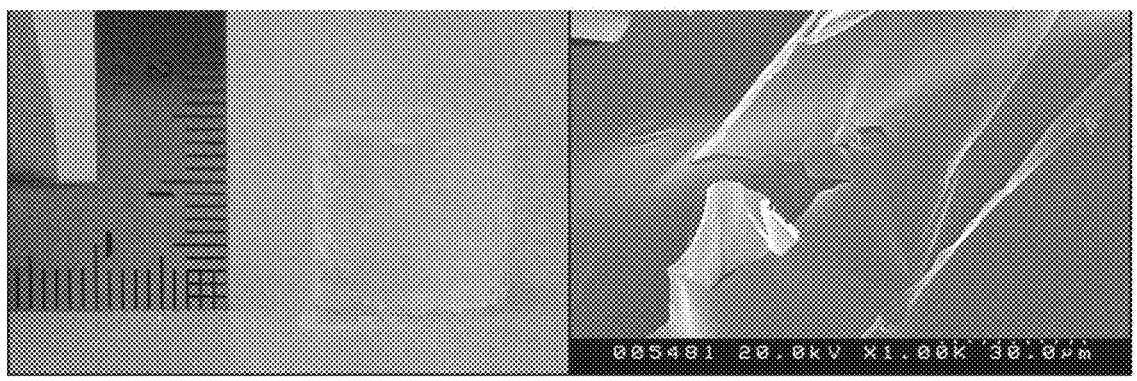
FIG. 10 is a photograph of the hydrogel made from the source TEMPO-oxidized cellulose.
FIG. 11 is a SEM micrograph showing the structure of the source TEMPO-oxidized cellulose.

Microfeatures of the cellulose before (FIGS. 4 and 5) and after gelation of (FIGS. 6 and 7) of sulfonated CNCs via chemical crosslinking was visualized using scanning electron microscopy (SEM). During gelation, chemical crosslinking will react with available hydroxyl groups or with functionalized groups to crosslink the cellulose. The sulfonated CNCs started out as micron-sized particles. The micrograph of CNC gel showed porous networks of CNC sheets, which is indicative of porous crosslinked hydrogels.

Microfeatures of the TEMPO-oxidized CNF hydrogels before (FIGS. 8 and 9) and after gelation (FIGS. 10 and 11) with metal-ions is shown in FIGS. 8-11. The TEMPO-oxidized CNF starts as low-density fibrous clumps. The CNF gel showed tighter packed sheets compared to its initial form, which is not unexpected given that its crosslinking occurs via ionic interactions as opposed to physical chemical bonds. It is important to note that the structures of the gels may not have been maintained during SEM because the gels had to be lyophilized prior to evaluation by SEM.

Figure 12A:
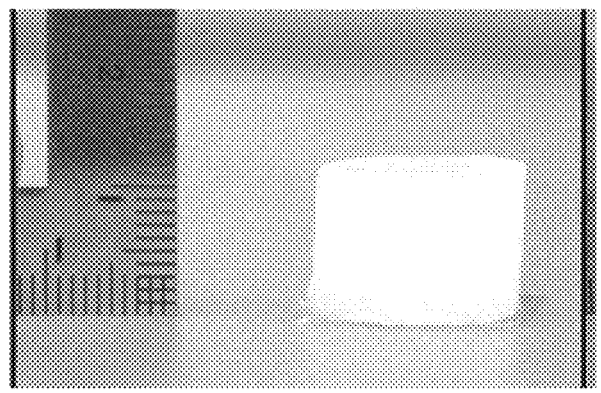
FIG. 12A shows a sample of the cellulose sulfate hydrogel from FIG. 2B and FIGS. 12B and 12C show the result of soaking the sample of FIG. 12A in two different fluids.
Figures 12B, 12C:
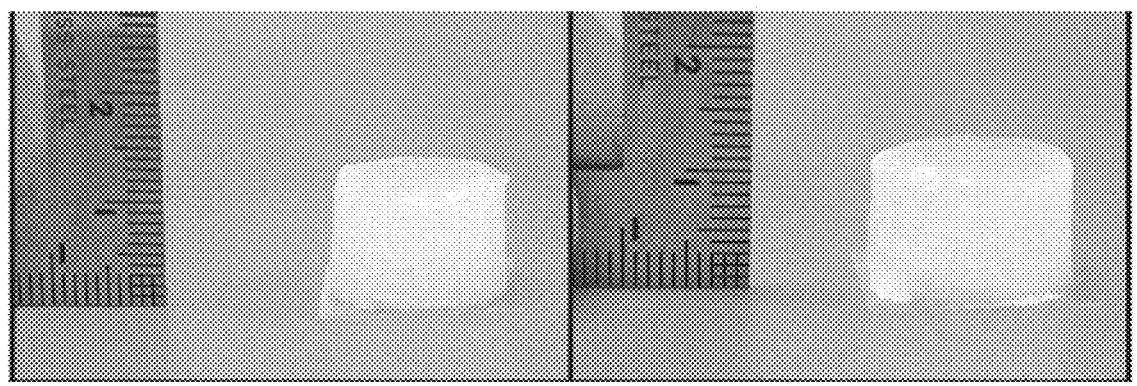
FIG. 12B shows the hydrogel after soaking in PBS for 7 days.
FIG. 12C shows the hydrogel after soaking in deionized water for 7 days.

To determine what degradation or swelling may occur in these nanocellulose hydrogels, each sample was weighed and measured before and after soaking in PBS or DI for seven days. FIG. 12A shows a sample of the cellulose sulfate hydrogel from FIG. 2B and FIGS. 12B and 12C show the result of soaking the sample of FIG. 12A in two different fluids. FIG. 12B shows the hydrogel after soaking in PBS for 7 days; FIG. 12C shows the hydrogel after soaking in deionized water for 7 days. In PBS, CNC hydrogels were fairly stable, maintaining their shape. However, the CNC hydrogels in DI became more brittle, which can be seen in the loss of shape (FIGS. 12A-12C).

Conversely, TEMPO-oxidized CNF hydrogels exhibit no change in structural integrity in PBS or DI (FIGS. 13A-13C). FIG. 13A shows the TEMPO-oxidized CNF hydrogel from FIG. 3C in two different fluids and FIGS. 13B and 13C show the result of soaking the sample of FIG. 13A in two different fluids. FIG. 13B shows the hydrogel after soaking in PBS for 7 days; FIG. 13C shows the hydrogel after soaking in deionized water for 7 days.

Each hydrogel was weighed in air and water to obtain density via Archimedes principle. The density of the hydrogel can be calculated using the following equation:

$$\rho = \frac{M_{air}}{M_{air} - M_{water}}(\rho_0 - \rho_L) + \rho_L \quad \text{(Eq. 1)}$$

where $\rho$=density of the sample, $M_{air}$=mass of the sample in air, $M_{water}$=mass of the sample in water, $\rho_0$=density of water, and $\rho_L$=density of air.

Figure 14:
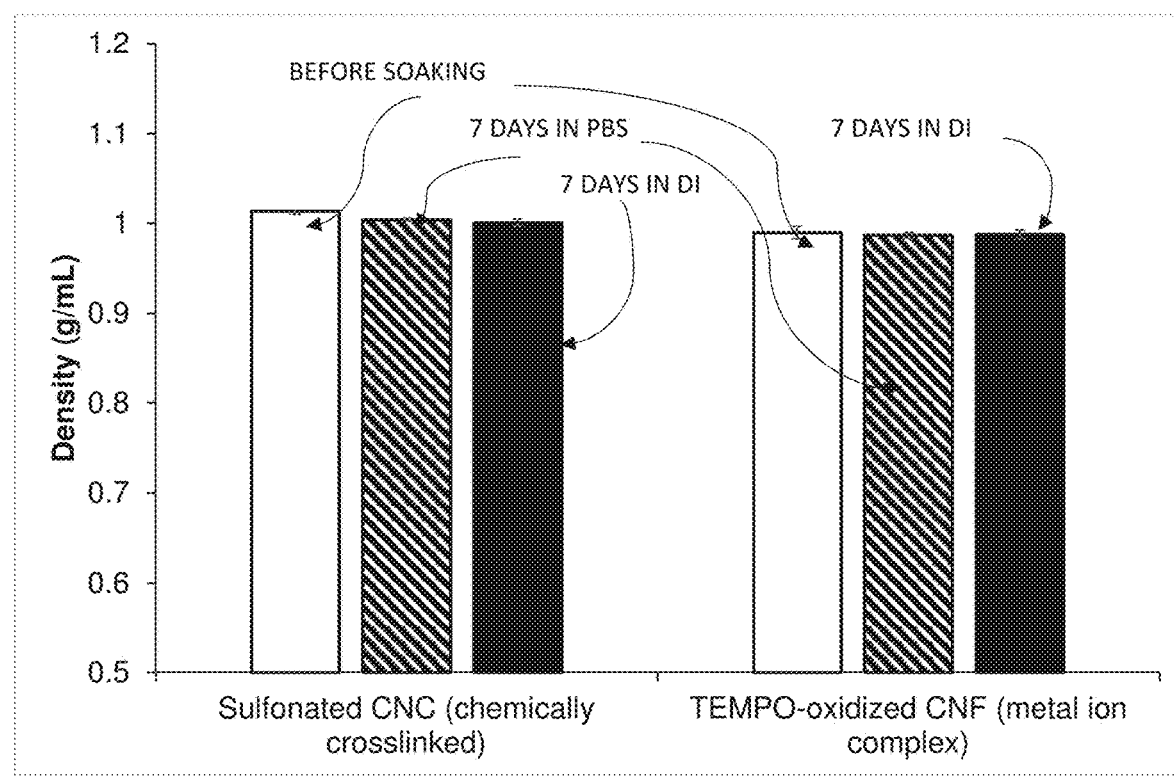
FIG. 14 is a bar graph showing the density measurements of hydrogels formed from chemically crosslinked CNC hydrogel and metal ion complexed TEMPO-oxidized cellulose hydrogel prior to soaking in fluids and after soaking in PBS or DI water for seven days. Values are average±standard error.

A decrease in density can occur if hydrogels swell, increase in water weight, or degrade. By evaluating changes to the hydrogel using density instead of mass, errors induced by handling and damage to the hydrogel are mitigated. FIG. 14 is a bar graph showing the density measurements of chemically crosslinked CNC hydrogels and metal ion complexed TEMPO-oxidized CNF hydrogels prior to soaking in fluids and after soaking in PBS or DI water for seven days. Values are average±standard error. Generally, the average density was slightly lower after the hydrogels soaked in DI water for seven days, for all hydrogel types. Changes in density were not statistically significant, which indicates that the hydrogels are stable in PBS and DI water. They exhibit no signs of swelling. However, the brittleness of sulfated CNC after exposure to DI water may be related to pH. Due to its low ionic strength, DI water has no buffering capabilities. Carbon dioxide from the atmosphere readily dissolves in DI water, forming carbonic acid and giving the DI water a pH of about 5.5. The slightly acidic nature may negatively impact the structure of cellulose because cellulose is digested by acid.

Figure 15A:
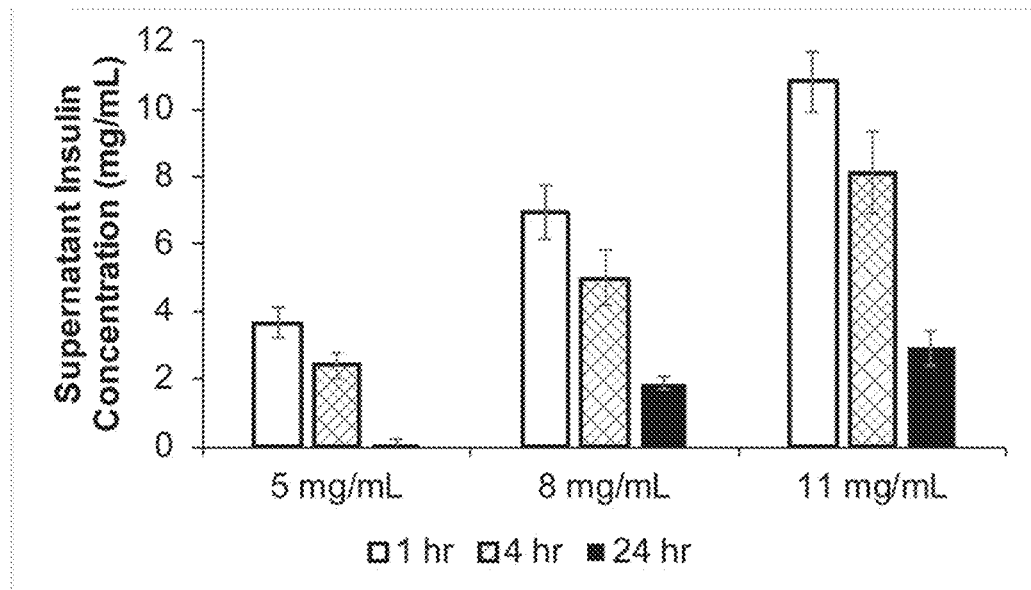
FIGS. 15A and 15B are graphs illustrating supernatant insulin concentrations during encapsulation (FIG. 15A) and corresponding insulin loading efficiency (FIG. 15B) for sulfated CNC hydrogel.
Figure 15B:
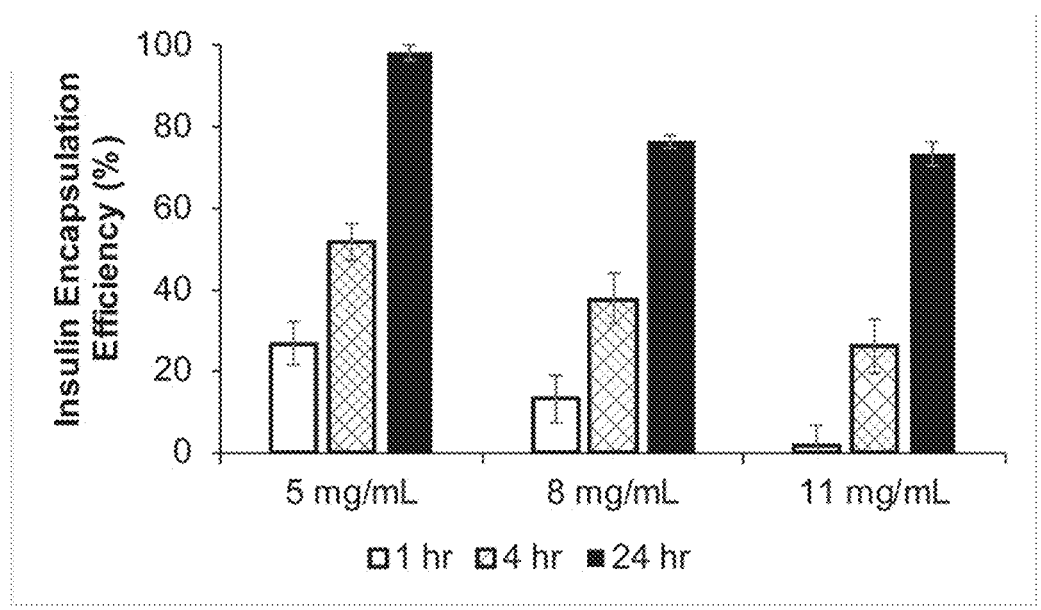

Insulin was selected as a relevant large hydrophobic protein to evaluate loading and release in PBS. Insulin was loaded by soaking hydrogels in solutions containing 5 mg/mL, 8 mg/mL, or 11 mg/mL insulin. Aliquots of the supernatant solution were collected at specified timepoints and evaluated using a Coomassie Blue Bradford Protein Assay in order to quantify the amount of insulin present. As the hydrogel encapsulates the insulin, the amount of insulin in the solution should decrease. FIGS. 15A and 15B are graphs illustrating supernatant insulin concentrations during encapsulation (FIG. 15A) and corresponding insulin loading efficiency (FIG. 15B) for sulfated CNC hydrogel. FIGS. 15A and 15B shows results for the loading of insulin in sulfated CNC hydrogel. At each insulin concentration, insulin within the solution steadily decreases, which suggests that insulin was incorporated into the hydrogel.

Insulin encapsulation efficiency was calculated as $$E = \frac{c_i - c_f}{c_i} * 100\% \quad \text{(Eq. 2)}$$

where E is the encapsulation efficiency, $C_i$ is the initial insulin concentration in solution, and $C_f$ is the concentration of insulin measured in solution at each timepoint.

After 24 hours, the encapsulation efficiency was 98.15±1.85% for 5 mg/mL, 76.51±1.60% for 8 mg/mL, and 73.53±2.79% for 11 mg/mL. This indicates that the hydrogels contain roughly 4.9 mg/mL, 6.12 mg/mL, and 8.09 mg/mL of insulin for 5 mg/mL, 8 mg/mL, and 11 mg/mL initial concentrations, respectively.

Figure 16:
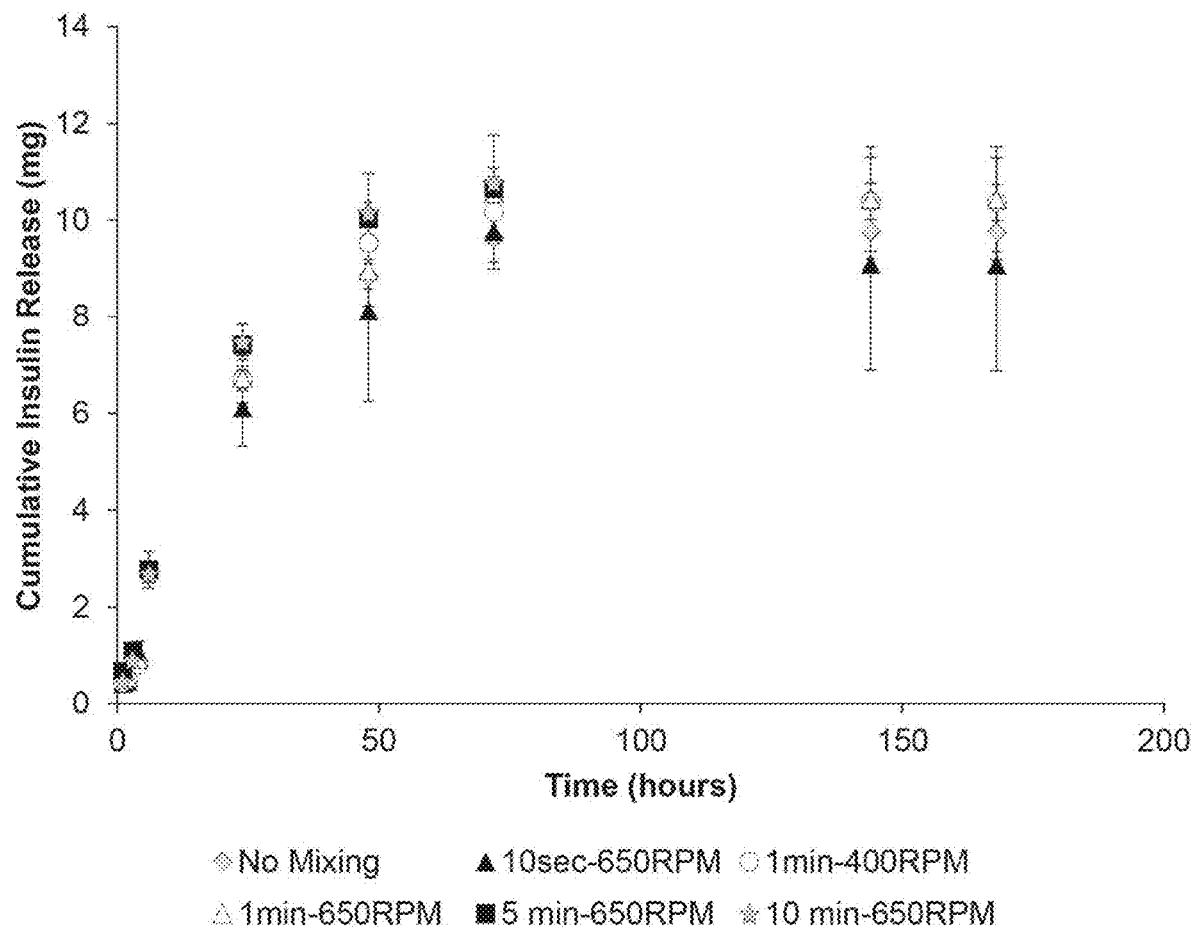
FIG. 16 is a graph comparing the insulin release profile for sulfated CNC hydrogels made with no mixing, 10 sec mixing at 650 rpm, 1 min mixing at 400 rpm, 1 min mixing at 650 rpm, 5 min mixing at 650 rpm and 10 min mixing at 650 rpm.

FIG. 16 is a graph comparing the insulin release profile for sulfated CNC hydrogels made with no mixing, 10 sec mixing at 650 rpm, 1 min mixing at 400 rpm, 1 min mixing at 650 rpm, 5 min mixing at 650 rpm and 10 min mixing at 650 rpm. The insulin concentration selected for further testing was 8 mg/mL. The effect of stirring speed and duration after addition of crosslinker is shown in FIG. 16. Increasing mixing speed and/or duration result in an increased release rate. This suggests that increased mixing speed and/or duration results in an increase in porosity and permeability of the hydrogel. This is significant because the hydrogel can be optimized for delivery of drugs or proteins of varied sizes. This also allows for tunable release profiles to optimize release in therapeutic concentrations.

Figure 17A:
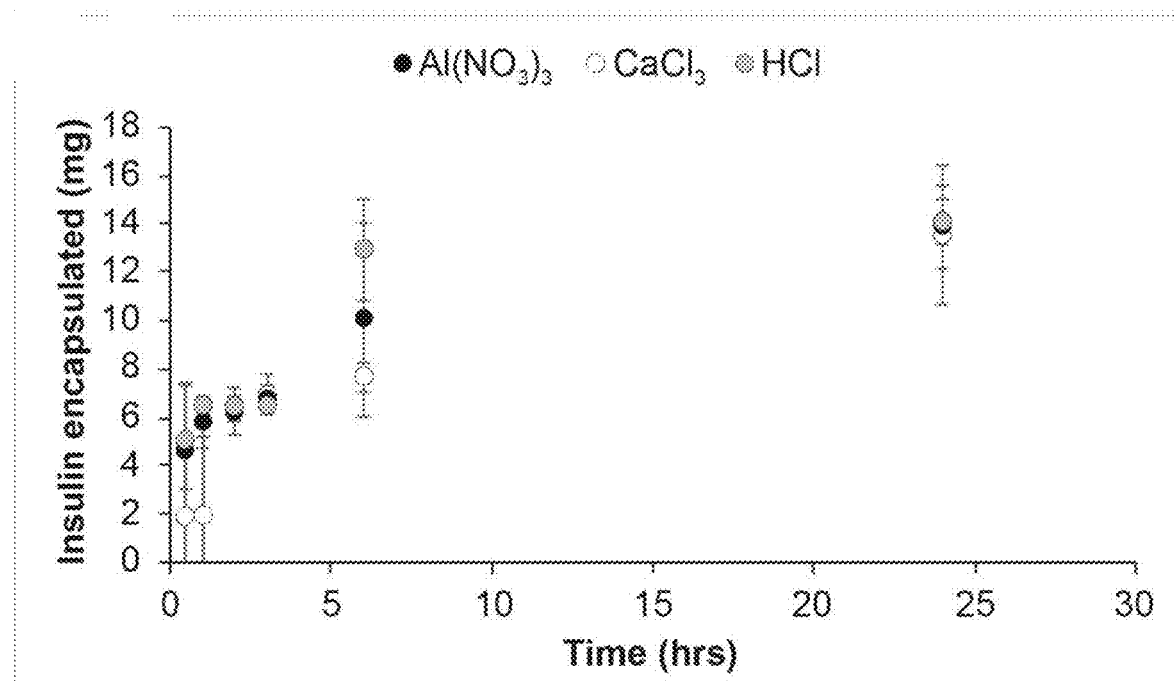
FIGS. 17A and 17B are graphs comparing insulin encapsulation (FIG. 17A) and cumulative insulin release (FIG. 17B) for TEMPO-oxidized CNF hydrogels made with aluminum nitrate ($Al(NO_3)_3$), calcium chloride ($CaCl_2$), or hydrochloric acid (HCl).
Figure 17B:
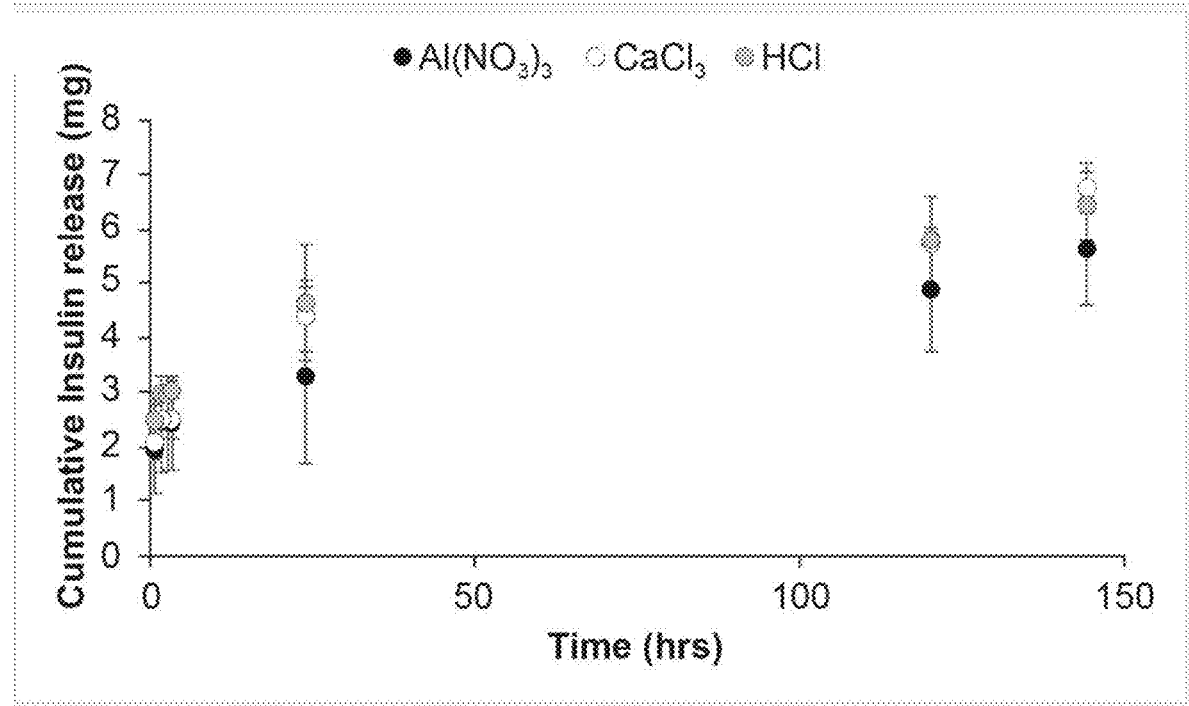

FIGS. 17A and 17B are graphs comparing insulin encapsulation (FIG. 17A) and cumulative insulin release (FIG. 17B) for TEMPO-oxidized CNF hydrogels made with aluminum nitrate ($Al(NO_3)_3$), calcium chloride ($CaCl_2$), or hydrochloric acid (HCl). The effects of metal ion selection for TEMPO-oxidized CNF hydrogels are shown in FIGS. 17A and 17B. As a trivalent cation $Al^{3+}$ creates hydrogels with this highest strength and lowest porosity and permeability. As a result, CNF hydrogels made with aluminum nitrate ($Al(NO_3)_3$) exhibit the lowest release rate for insulin. The divalent $Ca^{2+}$ exhibited loading and release rate between $Al^{3+}$ and $H^+$, as expected. HCl resulted in the mechanically weakest hydrogel. While CNF gels made with HCl loaded the fastest, they also released the fastest. By selecting ion crosslinkers by size and valency, hydrogel strength and permeability can be tuned, making this network highly favorable for encapsulation of a variety of drugs.

The onset of thermal changes of the sulfated cellulose hydrogels has been determined by differential scanning calorimetry (DSC). Each sample was scanned from −25° C. to 100° C. at a rate of 5° C./min. The DSC measurements were made on the cellulose, the cellulose hydrogel and the freeze-dried hydrogel samples (with and without loading PB in the hydrogels). About 5-15 mg of sample was cut (excess water was wiped off with a Kimwipe from the hydrogels), placed in an aluminum pan and sealed. The sample pan was heated alongside an empty pan as a reference.

Figure 18A:
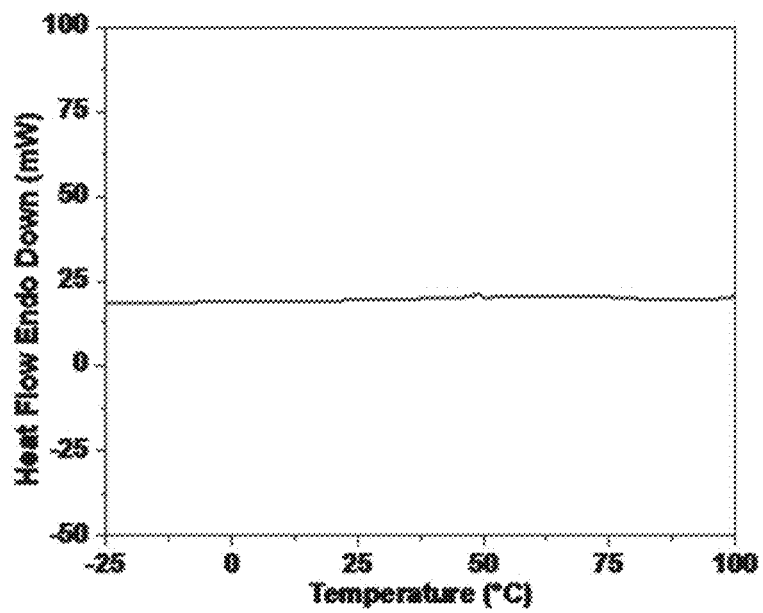
FIGS. 18A, 18B and 18C are graphs of Differential Scanning calorimetry tests performed from −25° C. to 100° C.
Figure 18B:
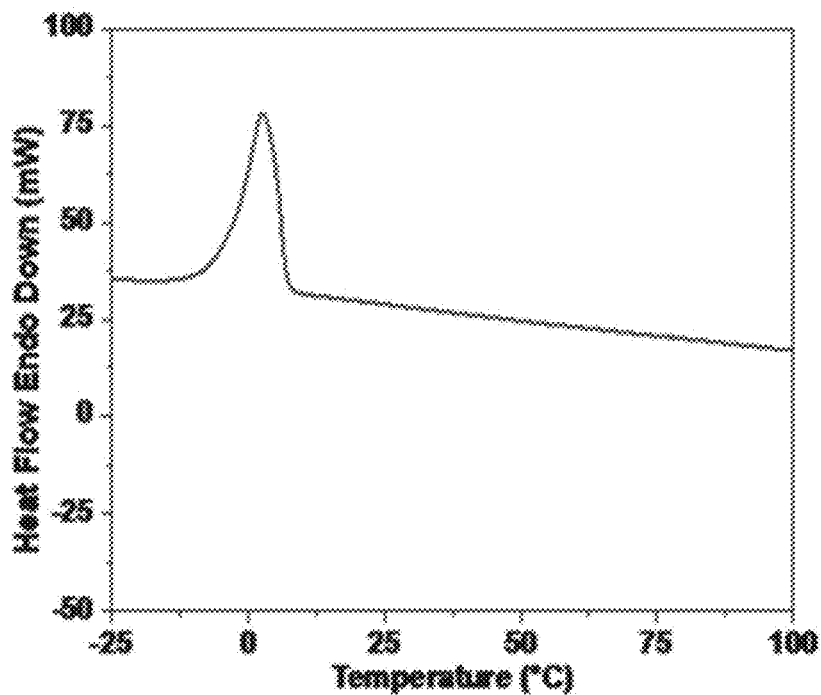
Figure 18C:
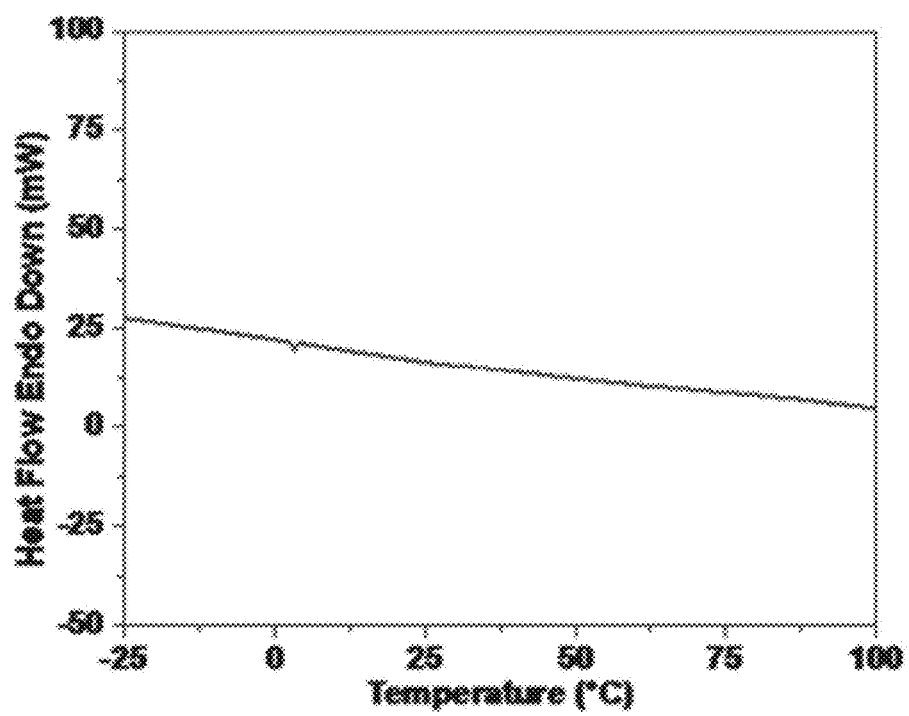

FIGS. 18A, 18B and 18C shows DSC thermographs for cellulose sulfate, cellulose sulfate hydrogels, and freeze-dried cellulose sulfate gels, respectively. The DSC was performed from −25° C. to 100° C. FIG. 18A is the DSC for commercial cellulose powder; FIG. 18B is the DSC for hydrogel made with commercial cellulose powder and FIG. 18C is the DSC for gel from FIG. 18B after freeze drying.

The cellulose source, FIG. 18A, did not show any peaks (endothermic changes) in the tested temperature range. The cellulose hydrogel, FIG. 18B, showed an endothermic phase transition around 0° C. which relates to the phase change of the free water present in the interstitial space of the hydrogel. Further, the negative slope from 50° C. to 70° C. corresponds to the breaking of the hydrogen bonds between water molecules (of cellulose-bound water) and the cellulose.

Figure 19A:
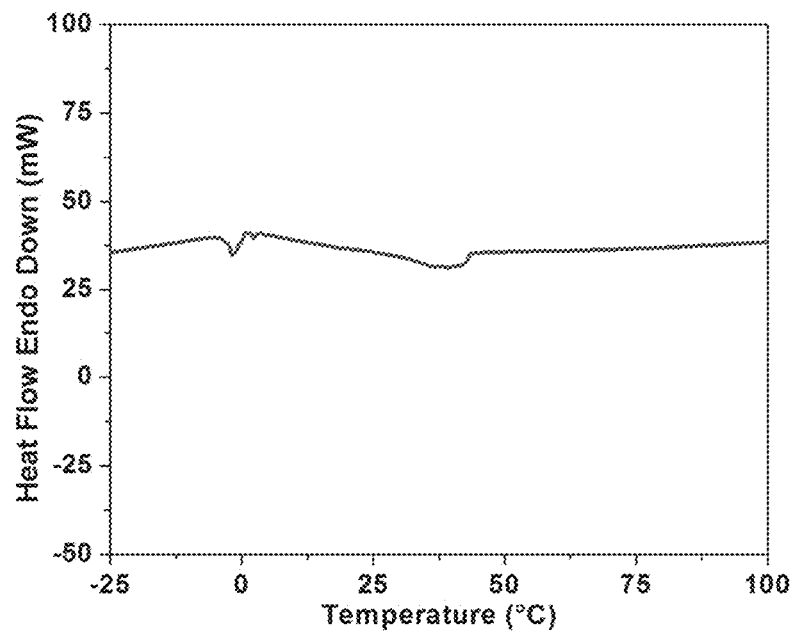
FIGS. 19A and 19B are graphs of Differential Scanning calorimetry tests performed from −25° C. to 100° C.
Figure 19B:
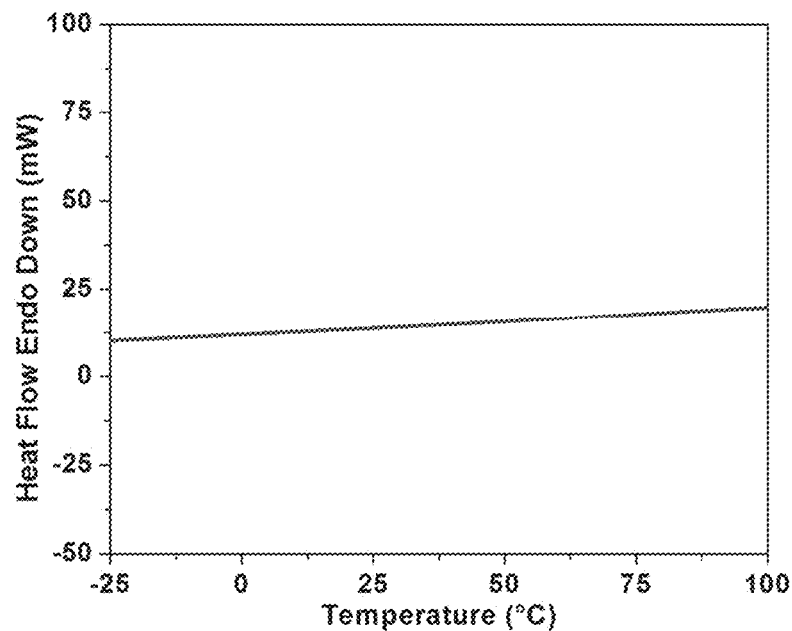

FIGS. 19A and 19B are graphs of Differential Scanning calorimetry tests performed from −25° C. to 100° C. FIG. 19A is the DSC for PB powder and FIG. 19B is the DSC for freeze-dried gel with PB encapsulated therein. FIG. 19A shows the thermograph of PB. Because of the hygroscopic nature of PB, there is a peak at 0° C. corresponding to the phase change of the water molecules. The rate of hydration of PB changes with increasing temperature, which corresponds to the soft peak between 25° C. and 50° C. The thermal scans on the freeze-dried hydrogels, both without PB (FIG. 18C) and PB loaded (FIG. 19B), did not show any endothermic changes (peaks). Therefore, it was concluded that the freeze-dried form of the hydrogel is stable (i.e., there is no structural change, bond breaking) in the tested temperature range.

To further improve the hydrogel release kinetics, the structure of the hydrogel was modified to change the hydrogel structure and mechanical properties by changing the concentration of the NaOH solution added to the hydrogel. An increase in alkalinity increased the qualitative mechanical strength of the hydrogel, and a decrease in alkalinity decreased the mechanical strength of the hydrogel. It is believed that this plays an important role in the encapsulation and the release properties of PB, as the mechanical strength of the hydrogel affects the pore sizes in the hydrogel. By tuning the pore size and gel crosslinking, the release profile of entrapped drug molecules can be tuned.

Figure 20A:
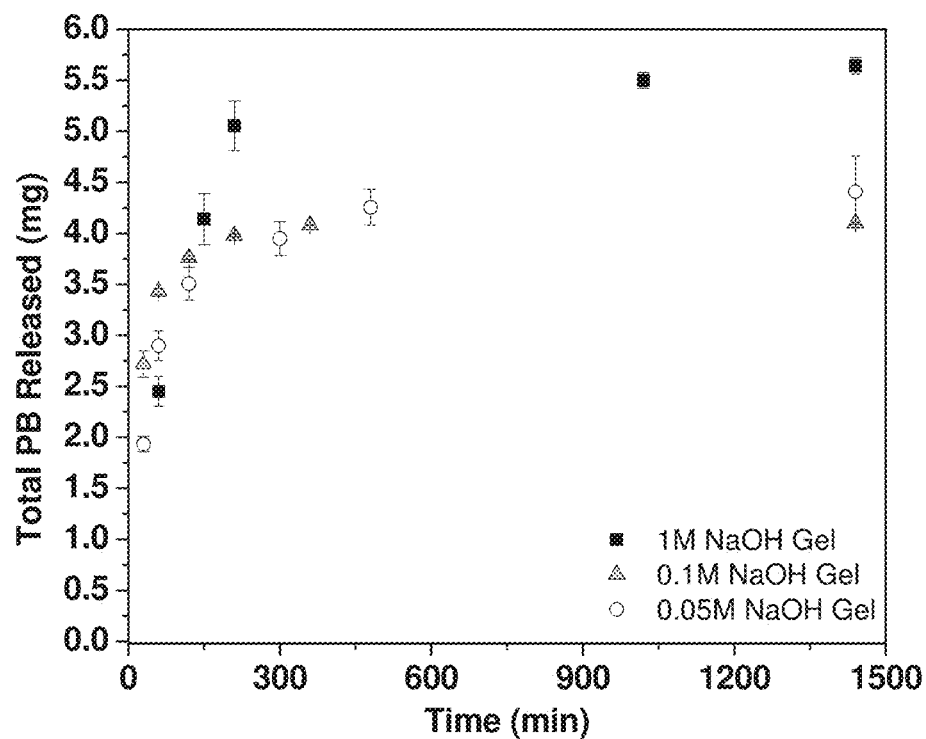
FIGS. 20A and 20B are graphs showing the dependence on NaOH concentration on PB release from hydrogels over a period of time where
Figure 20B:
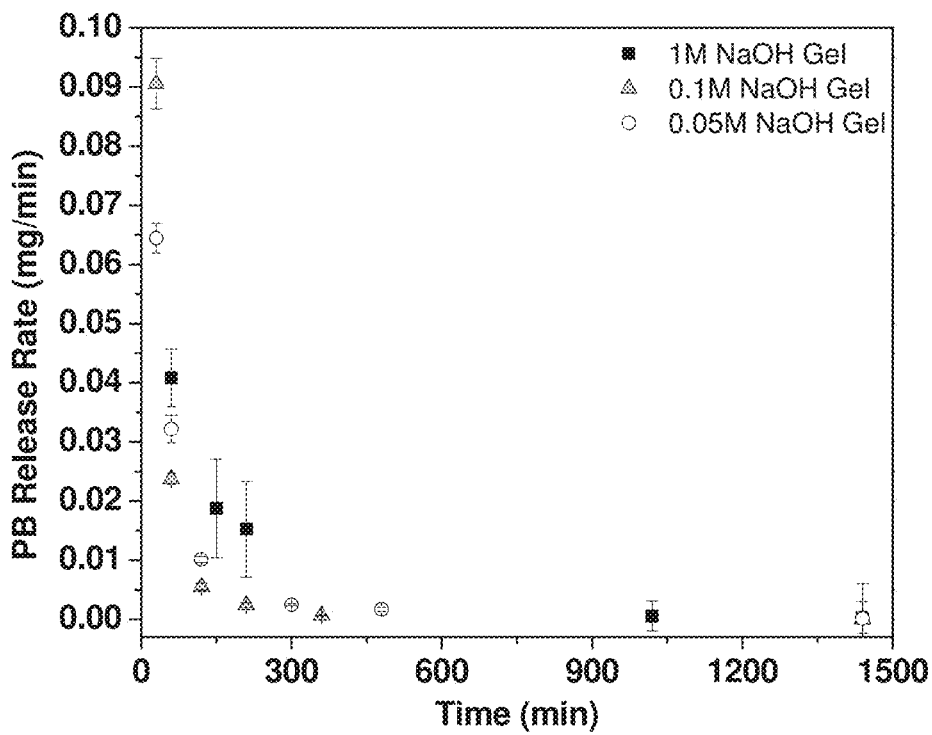

To observe this effect, hydrogels were made using three different concentrations of NaOH: 50 mM, 0.1 M, and 1 M. FIGS. 20A and 20B are graphs showing the dependence on NaOH concentration on PB release from hydrogels over a period of time where FIG. 20A illustrates the total amount of PB released after an allotted time and FIG. 20B illustrates the rates of release at different time points for the different concentrations of NaOH hydrogels.

The 50 mM and 0.1 M hydrogels behaved similarly in both loading and releasing due the fact that the pH difference is only about 0.3 (from pH 12.7 to pH 13). However, a change from 0.1 M to 1 M resulted in a pH increase of 1 (pH 13 to pH 14). FIGS. 20A and 20B illustrate the release of PB in the different hydrogels. The hydrogel with 1 M NaOH had largest quantity of encapsulated PB, however there was no significant difference in release kinetics between each of the samples. While the release rate for hydrogels made with 1 M NaOH was slightly slower, all the encapsulated PB was released after 24 hours, as with the other hydrogels. However, the slightly slower release rate for hydrogels made with 1 M NaOH indicates that further optimization and increase in NaOH concentration may yield hydrogels with a more desirable PB release profile.

By modifying the hydrogel formation protocol to include the addition of β-Cyclodextrin during the synthesis of the hydrogel, productivity increased tremendously. This change enabled the hydrogel to load PB much faster. Lyophilization was used on the β-cyclodextrin infused hydrogels to increase the hydrophilic nature of cellulose by dehydrating it. The hydrogels absorb the liquid, PBS in this case, and loads PB into the hydrogel. The liquid level is reduced; however, the amount of PB in the liquid is still the same as prior to adding to the hydrogel. 2 mg/mL PB in PBS was used in order to preserve the amount of available materials.

Figure 21A:
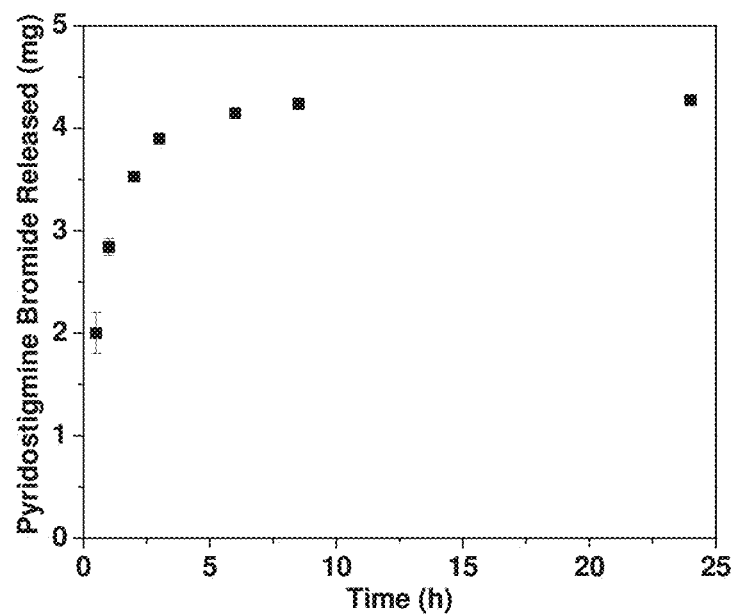
FIGS. 21A and 21B are graphs which show PB released from the formulated hydrogel as a function of time.
Figure 21B:
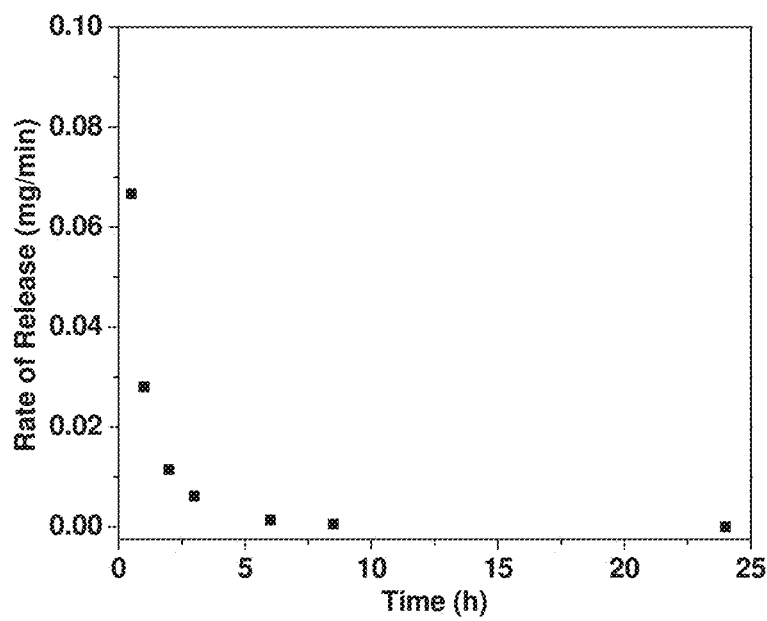

FIGS. 21A and 21B are graphs showing the release profile of PB where FIG. 21A shows the kinetic release profile of PB from hydrogel into a PBS solution and FIG. 21B shows the corresponding rate of release—for the same versus time. FIGS. 21A and 21 B illustrates the release of PB in two ways. FIG. 21A shows that the release rate initially is fast, but slows significantly after the first hour, and then slowly reaches maximum PB released between 8.5-24 hours. FIG. 21B shows the derivative of the graph in FIG. 21A. This derivative shows the rate of release versus time, displaying effectively an inverse of the graph in FIG. 21A. The current protocol displays an exponential decay release rate profile, which means that the only near-linear portions are in the beginning and at the end of the release.

Figure 22:
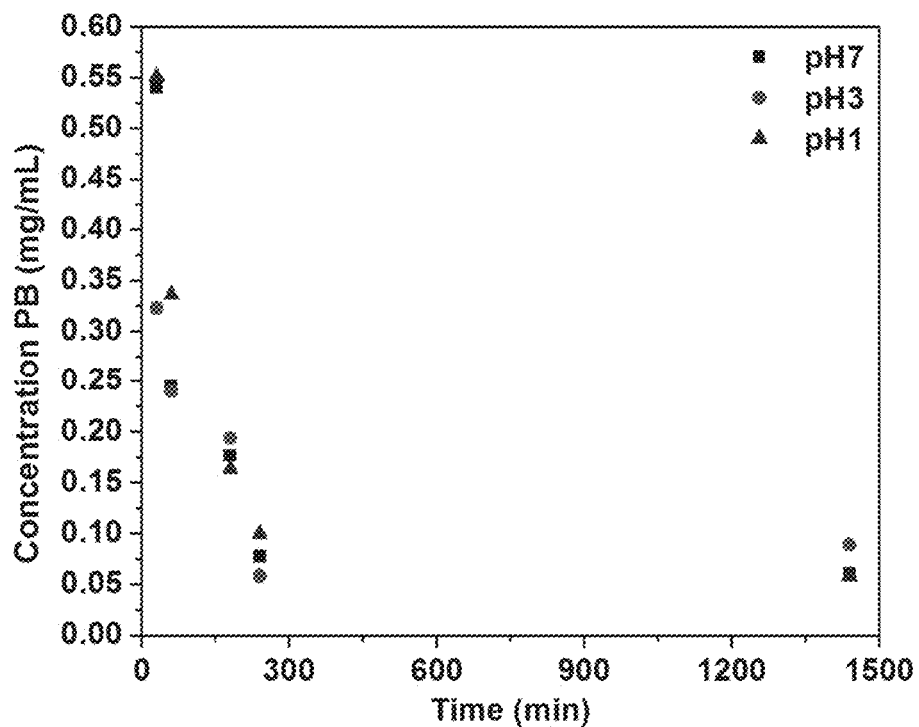
FIG. 22 is a graph showing the effect of pH on PB release from CNC hydrogels. A range of acidic pHs was evaluated to mimic effects of stomach acid. No significant difference was observed.

The release of PB into an acidic environment, such as the gastrointestinal system, was tested to determine pH stability of the hydrogel and the release rate. Since stomach acid is composed of HCl, we chose to use HCl dilutions in PBS to vary the pH of the solution. We chose to evaluate the performance at three different pH's, pH 1, pH 3, and pH 7, to simulate performance in the normal acidity range of the human stomach versus performance in pure PBS. The performance of the CNC-PB samples are shown in FIG. 22 showing the effect of pH on PB release from a CNC hydrogels. A range of acidic pH was evaluated to mimic effects of stomach acid. No significant differences were observed. The results displayed very similar trends across the board. At each of the evaluated pH's, the hydrogels behaved similarly, which is beneficial as the desired application for the drug system is oral ingestion. This test also shows the sturdiness of the hydrogels in an acidic environment. The lack of ability in humans to enzymatically breakdown cellulose means that the cellulose retains most of its mechanical integrity during the drug release in acidic environments.

Figure 23:
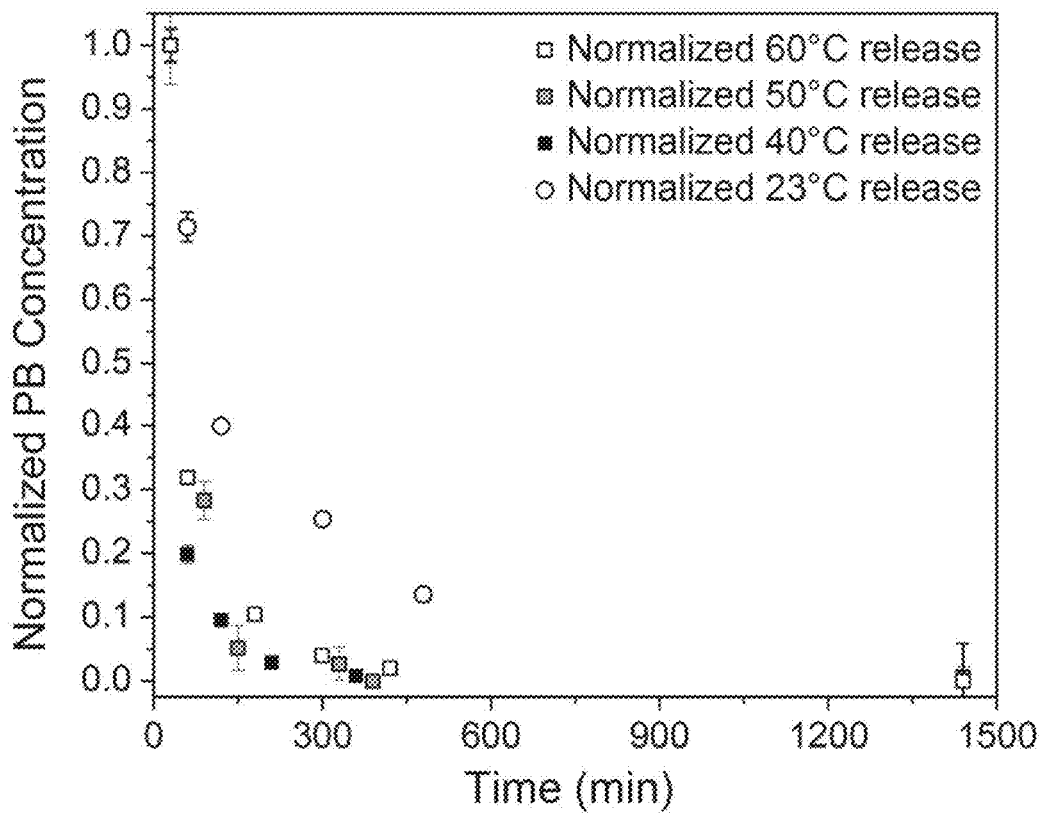
FIG. 23 is a graph showing concentrations of normalized PB release from CNC hydrogels at different temperatures.

To illustrate that the hydrogel and PB were stable at high temperatures, samples were held at elevated temperatures for an extended period. FIG. 23 is a graph showing concentrations of normalized PB release from CNC hydrogels at several temperatures. The hydrogels were placed in closed scintillation vial and the vial was wrapped with Teflon tape and Parafilm to seal the vials. The vials were then placed in an incubator at 40° C. for 5 days. After the 5 days, one sample was removed, and the release profile was determined. The other vials were left in the incubator and exposed to 50° C. for another 6 days. After 6 days at 50° C., one sample was removed, and the incubator was set to 60° C. for the final sample. FIG. 23 shows the normalized release profiles. All the elevated temperature samples displayed the same release profile; however, all the hydrogels that were exposed to an elevated temperature had a faster release profile than the room temperature sample.

Figure 24:
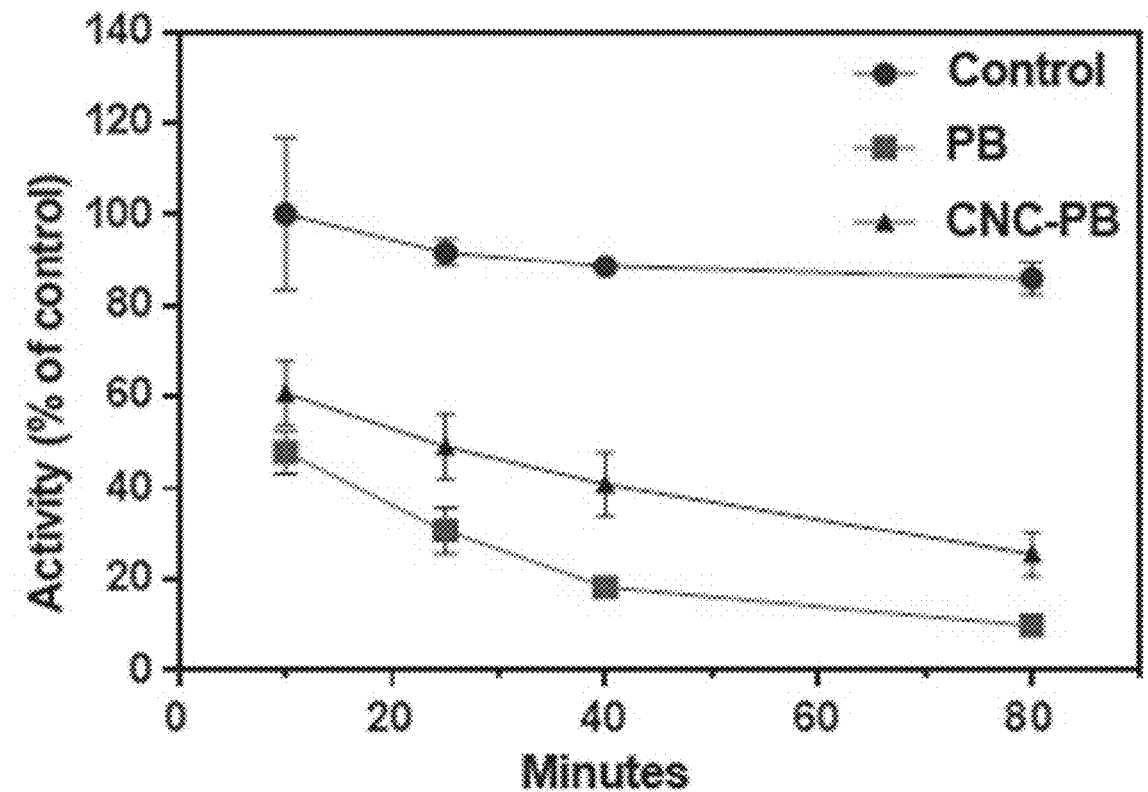
FIG. 24 is a graph showing the radiometric AChE assay results of in-vitro AChE activity after exposure to free PB and CNC-PB.

A radiometric assay was done to evaluate acetylcholinesterase (AChE) Inhibition with both free PB and CNC-PB. FIG. 24 is a graph showing the radiometric AChE assay results of in-vitro AChE activity after exposure to bare PB and CNC-PB. FIG. 24 illustrates time-dependent inhibition of mouse blood AChE activity by free PB and encapsulated PB. It was found that AChE activity was significantly different among the groups tested (PBS, free PB and hydrogel encapsulated PB). When compared to free PB, the PB loaded into the hydrogel (CNC-PB) showed significantly longer inhibitory effect (p<0.001) but lower intensity of inhibition (p<0.001). There was also no significant interaction between inhibitory effect and time (p=0.3597). While multiple comparisons indicated AChE, activity was lower with both the PB and PB-loaded hydrogel (CNC-PB) compared to PBS at all time-points, there were no significant time-dependent differences comparing the two different pyridostigmine conditions (PB vs CNC-PB).

This data shows a trend of in-vitro differences in the timing of AChE inhibition when either free pyridostigmine or pyridostigmine in CNC was added to a tissue (mouse blood) and incubated at 37° C. While limited by the number of replicates (n=3 independent assays) and by the assay conditions (i.e., the enzyme reaction lasted for 8 minutes during which pyridostigmine could have been released from the hydrogel to act as free pyridostigmine), the data suggest that inhibition was delayed and prolonged by PB in the hydrogel.

When these data were evaluated using non-linear curve fitting with a 2-phase exponential decay (i.e., to elucidate the initial more rapid inhibition of AChE vs the apparent later inhibition), some insight into the relative effects of PB source (free vs hydrogel) were obtained. The $R^2$ values for the two nonlinear curves were 0.88 and 0.65 for free pyridostigmine and CNC-hydrogel, respectively. When half-life for early and later decay phases between free and hydrogel-PB were compared ($T_{1/2}$ early phase: PB=13.1 min, CNC hydrogel=4.9 min; $T_{1/2}$ late phase: PB=17.3 min, CNC hydrogel=55 min.), it was noted that both the fast (early) and slow (late) phase of inhibition was different. Of interest the late phase was prolonged from 17.3 minutes with free pyridostigmine to 55 minutes with the encapsulated PB. This suggests that PB was being released from the hydrogel in its interaction at 37° C. with the tissue in vitro to prolong AChE inhibition.

Performance of free-PB and CNC-encapsulated PB was evaluated in-vivo through time-dependent inhibition by free vs. CNC-encapsulated PB by first estimating maximum tolerated (i.e., non-lethal) doses (MTDs) for each. Signs of cholinergic malfunction include salivation, lacrimation, urination, and defecation, which is often given the acronym, SLUD. Mice were observed and SLUD signs were used to rank reaction on the following scale: 0=no signs; 1=very slight signs such as possible fasciculations, piloerection; 2=slight toxicity including mild fasciculations, salivation or lacrimation; 3=moderate signs such as moderate head and neck area tremors, tail "twitching" and more obvious fasciculations and/or SLUD signs; 4=severe signs, notable whole body tremors, prostrate/reduced ambulation, extensive fasciculations, and/or SLUD signs, occasional choreatic movements; and 5=death.

MTDs were estimated using the up-and-down method, treating 1-3 mice at a time and observing functional cholinergic toxicity signs and lethality out to 24 hours. Young adult male CD1 mice (about 35-40 g at time of dosing) were purchased from Charles River and acclimated to the AAALAC-accredited facility at OSU for at least one week before conducting toxicity studies. A solution of free PB was made in PBS at 13.33 mg/ml and used for all PB dosing, adjusting dosing volume accordingly for each dose. Contents of a vial of lyophilized CNC gel (65 mg wet weight) containing 40±5 mg pyridostigmine were first disrupted by mortar and pestle and then rehydrated by adding 3 ml PBS to obtain a putative PB concentration of 13.33 mg/ml. An aliquot of the freshly prepared gel was administered by gavage tube, adjusting dosing volume as with the free pyridostigmine. All gavage treatments were finished within 1-3 minutes of hydrating the gel. Doses evaluated in pyridostigmine and/or pyridostigmine-CNC gel were 20 mg/kg, 39.5 mg/kg, 51.3 mg/kg, 66.7 mg/kg, 86.7 mg/kg and 112.7 mg/kg.

One mouse was first treated with the highest dose of pyridostigmine (112.7 mg/kg). It showed severe signs and death within one minute. A second mouse was treated with 51.3 mg/kg showed minimal to moderate signs at 18-20 minutes, but then overt whole-body tremors were noted within a half hour and clonic seizures and death occurred at about 50 minutes.

A third mouse treated with 39.5 mg/kg showed very slight to slight signs of a reaction for about the first 20 minutes, but then clear signs of toxicity (scores of ≥3) around 30 minutes after dosing, peaking with a functional score of 4 at 3-4 hours and then prostration, clonic seizures and death at the 270-minute time-point. Accordingly, lethality was noted with 112.7, 51.3 and 39.5 mg/kg PB doses.

A fourth mouse was then treated with 20 mg/kg pyridostigmine. Very slight to slight signs of toxicity were noted for the first half hour, followed by moderate signs (score=3) at the 45 min and 2-hour time-points. By 2.5 hours after dosing, no obvious functional signs were noted aside from lethargy. Thus, 20 mg/kg was defined as the MTD for free pyridostigmine.

Using the CNC-gel, a fifth mouse was treated with 20 mg/kg PB in gel. This mouse showed no signs for the first hour after dosing and continued to be sign free through 24 hours. Another mouse was treated with 86.7 mg/kg PB in gel. Within 60 minutes after dosing, this mouse showed obvious fasciculations, tail twitching and fine head and neck tremors (score=3). By 120 minutes, whole body tremors, tail twitching, SLUD signs and "puffy face" (suggesting congestion perhaps of salivary tracts), were noted. By 180 minutes, a fine whole-body tremor and prostrate positioning were noted. Interestingly, by 270 minutes, no classic cholinergic signs were noted (score=0), but the animal appeared in "poor" overall condition with dried secretions around the eyes and slow movement around the cage. He survived until the end of the observation period (24 hours).

Another mouse was given 66.7 mg/kg PB as CNC-gel. Marked whole body fasciculations were noted by one hour after dosing, along with mild tremors. At 120 minutes, the mouse showed fine tremors and tail twitching (score=3). By 180 minutes, fine, whole body tremors were noted along with apparent exhaustion/prostration. At the 267-minute time-point, clonic seizures were noted followed shortly by death.

Another mouse was then given 51.3 mg/kg PB in gel. By one hour, only very slight signs including mild fasciculations were noted (score=1). At 120 minutes, lesser fasciculations were noted but minor occasional tail twitching was observed (score 1-2). At 180 minutes, a score of 0.5 was given based on infrequent fasciculations, while by 170 minutes, no cholinergic signs were noted (score of 0.)

Figure 25A:
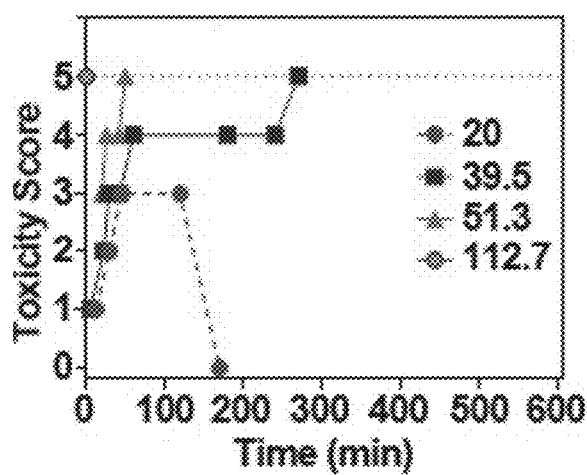
FIGS. 25A and 25B are graphs showing the toxicity score from mice MTD studies where
Figure 25B:
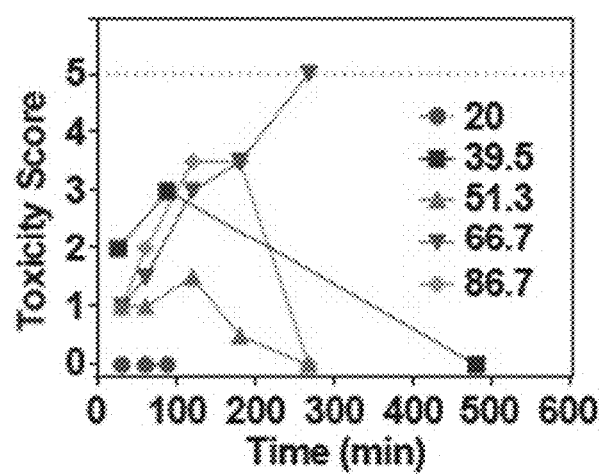

FIGS. 25A and 25B are graphs showing the toxicity score from mice MTD studies described above. FIG. 25A shows a PB dosage study and FIG. 25B shows a CNC-PB dosage MTD study. Functional signs of toxicity in all mice are shown in where FIG. 25A shows functional scores after pyridostigmine dosing, while FIG. 25B shows time-dependent responses after CNC gel dosing.

Figure 26A:
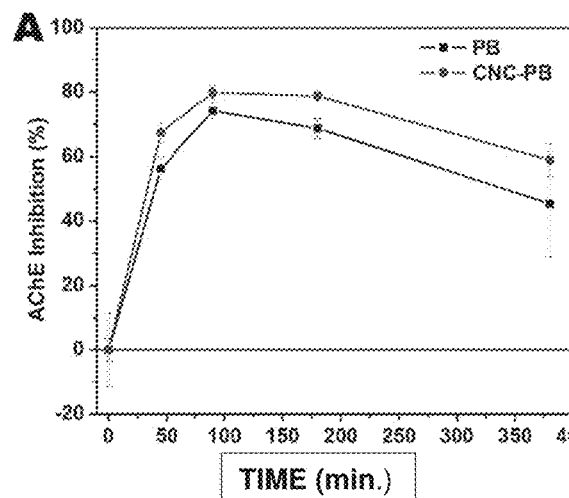
FIGS. 26A, 26B and 26C are graphs illustrating invivo acetylcholinesterase (AChE) inhibition for up to 400 minutes when dosed with 0.5×MTD (10 mg/kg) PB (FIG. 26A) or 0.3×MTD (6 mg/kg) FIG. 26B. Longer timepoints for AChE inhibition is shown after dosing with (C) 0.3×MTD (6 mg/kg) (FIG. 26C).
Figure 26B:
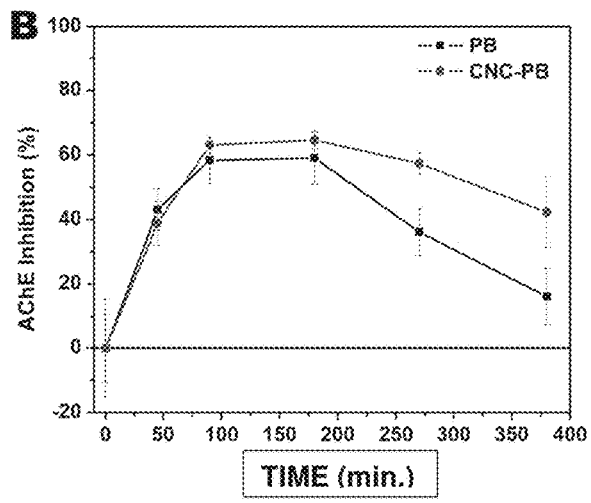
Figure 26C:
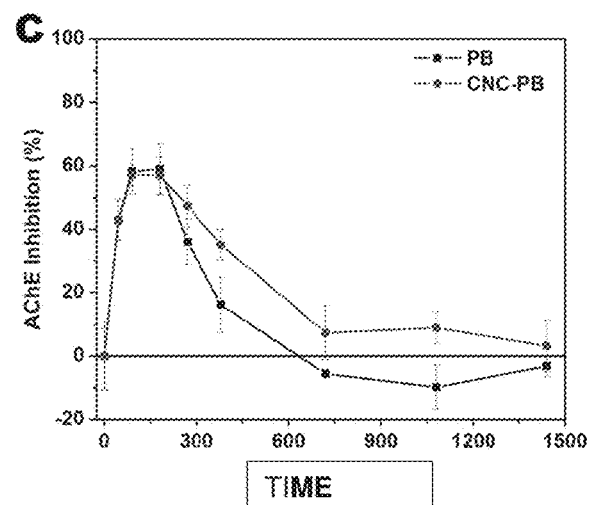

Pertinent observations for the in-vivo studies are that the MTDs for free pyridostigmine and CNC gel containing pyridostigmine were 20 mg/kg and 51.3 mg/kg, respectively. Our experience with anticholinesterases suggests that approximately 0.3-0.5 MTD doses will be non-lethal but elicit substantial blood AChE inhibition, suitable for kinetic evaluations. AChE inhibition over time when dosed with 0.5×MTD (FIG. 26A) and 0.3×MTD (FIG. 26B and FIG. 26C) shows improved longevity of pyridostigmine activity when encapsulated in sulfated CNC hydrogels.

Hydrogels made from sulfated CNCs and/or TEMPO-oxidized CNFs can also be tuned to provide an interconnected pore network suitable for 3D cell culture and guided tissue regeneration (Bačáková L1, Novotná K, Pařízek M. "Polysaccharides as cell carriers for tissue engineering: the use of cellulose in vascular wall reconstruction". *Physiologi-* cal Research. 2014, 63). The diameters of mammalian cells are typically in the range of 5 to 100+μm. (Diekjürgen D, Grainger D W. "Polysaccharide matrices used in 3D in-vitro cell culture systems. *Biomaterials*. 2017, 141, pp 96-115). It is known that the porosity and permeability of the CNC and CNF hydrogels can be tuned by altering environment pH, amount of CNC or CNF, and the amount and type of crosslinker as well as mechanical stimulation during formulation. A variety of freeze-thaw and freeze-drying protocols can also be used to change the pore size to make hydrated or freeze-dried CNC or CNF constructs for in-vitro cell culture. Additionally, constructs for guided tissue regeneration can also be produced. 3D cell culture has been shown to improve cell culture and function in-vitro because of the increased area for cell attachment and closer mimicry of native extracellular environments. (Wang J, Zhao L, Zhang A, Huang Y, Tavakoli J, Tang Y. "Novel Bacterial Cellulose/Gelatin Hydrogels as 3D Scaffolds for Tumor Cell Culture.", *Polymers*. 2018, 10, p. 581).

It is thus concluded that hydrogels from the sulfated CNCs and TEMPO-oxidized CNFs provide a robust and tunable excipient for a variety of drugs as demonstrated through controlled release of pyridostigmine bromide and insulin.

We claim:

1. A method of forming hydrogels containing a biologically active drug compound or therapeutic agent encapsulated therein for delivery to a patient,
   the hydrogels formed from cellulose-based materials selected from the group consisting of sulfated crystalline nano cellulose (CNC) and TEMPO (2,2,6,6-tetramethylpiperidine-1-oxyl radical) cellulose nanofibers (CNF) comprising
   i) forming cross-linked sulfated crystalline nanocellulose (CNC) using a basic solution and one or more chemical crosslinking agents, and
   ii) forming hydrogels with TEMPO (2,2,6,6-tetramethylpiperidine-1-oxyl radical) cellulose nanofibers (CNF) using an aqueous solution containing ionic crosslinking agents,
   said hydrogels formed by
   iii) hydrating the nano cellulose (CNC) or TEMPO (2,2,6,6-tetramethyl-piperidine-1-oxyl radical) cellulose nanofibers (CNF) under high-powered sonication to form a clear solution followed by
   iv) adding the chemical or ionic crosslinking agents to form a crosslinked hydrogel, comprising a fibrous network with an internal surface having pore sizes and permeability for encapsulation of the biologically active drug compound or therapeutic agent
   wherein the biologically active drug compound encapsulated is insulin and wherein the therapeutic agent encapsulated is pyridostigmine bromide, the insulin exhibiting controlled release from the crosslinked hydrogel of at least 48.5% of the encapsulated insulin over a 150 hour period and the pyridostigmine bromide exhibiting controlled release of 100% from the crosslinked hydrogel in a 24 hour period,
   said crosslinked hydrogels containing the insulin or pyridostigmine bromide formed by adding the insulin or pyridostigmine bromide to the crosslinked hydrogels.

2. The method of claim 1, wherein the ionic crosslinking agents cause metal-coordinated crosslinking of the TEMPO-oxidized cellulose.

3. The method of claim 1, wherein the hydrogel further includes one or more compounds that increase small molecule encapsulation.

4. The method of claim 3, wherein the one or more compounds comprises β-cyclodextrin.

5. The method of claim 2, wherein the ionic crosslinking agent is selected from a group consisting of aluminum nitrate, calcium chloride, sodium chloride, and hydrochloric acid.

6. The method of claim 1, wherein the pore size and permeability of the hydrogel is controlled by varying the mixing speed, mixing method, pH, and/or temperature or a combination thereof used during formation of the hydrogels.

7. The method of claim 1, wherein the pore size and permeability of the crosslinked hydrogel is controlled by selection of the one or more crosslinking agents.

8. The method of claim 1, wherein the crosslinked hydrogel produced is stable in humid environments and temperatures from −25° C. to 100° C.

9. The method of claim 1, wherein the insulin and pyridostigmine bromide and exhibit sustained release for an extended period of time.

* * * * *